(12) United States Patent
Kolmakov et al.

(10) Patent No.: US 11,738,312 B2
(45) Date of Patent: Aug. 29, 2023

(54) MULTIDIMENSIONAL PRINTER

(71) Applicant: Government of the United States of America, as represented by the Secretary of Commerce, Gaithersburg, MD (US)

(72) Inventors: Andrei A. Kolmakov, Frederick, MD (US); Glenn Emerson Holland, Rockville, MD (US); Tanya Gupta, Gaithersburg, MD (US)

(73) Assignee: GOVERNMENT OF THE UNITED STATES OF AMERICA, AS REPRESENTED BY THE SECRETARY OF COMMERCE, Gaithersburg, MD (US)

(*) Notice: Subject to any disclaimer, the term of this patent is extended or adjusted under 35 U.S.C. 154(b) by 334 days.

(21) Appl. No.: 16/944,571

(22) Filed: Jul. 31, 2020

(65) Prior Publication Data
US 2021/0031150 A1    Feb. 4, 2021

Related U.S. Application Data

(60) Provisional application No. 62/881,677, filed on Aug. 1, 2019.

(51) Int. Cl.
*B29C 64/00* (2017.01)
*B01D 69/12* (2006.01)
(Continued)

(52) U.S. Cl.
CPC ..... *B01D 69/125* (2013.01); *B01D 67/00045* (2022.08); *B01D 67/0088* (2013.01);
(Continued)

(58) Field of Classification Search
CPC .......................... B01D 69/125; B01D 67/0088
See application file for complete search history.

(56) References Cited

U.S. PATENT DOCUMENTS

| 5,674,346 A | 10/1997 | Kundel |
| 2004/0046120 A1* | 3/2004 | Moses ............ H01J 37/20 |
| | | 250/311 |

(Continued)

FOREIGN PATENT DOCUMENTS

CN    1974608 A    6/2007

OTHER PUBLICATIONS

Winkler, R., et al., "3D nanoprinting via focused electron beams", Journal of Applied Physics, 2019, p. 210901, vol. 125.
(Continued)

*Primary Examiner* — Nicholas R Krasnow
(74) *Attorney, Agent, or Firm* — Office of Chief Counsel for National Institute of Standards and Technology

(57) ABSTRACT

A multidimensional printer makes a multidimensional structure from a liquid composition and includes: an energetic crosslinking particle source; a vacuum chamber that receives energetic crosslinking particles from the energetic crosslinking particle source; a membrane that transmits the energetic crosslinking particles; and a sample chamber that: receives a liquid composition that includes a solvent and polymers, the polymers including a cross-linkable moiety subjected to the energetic crosslinking particles such that portions of the polymers proximate to the cross-linkable moieties subjected to the energetic crosslinking particles crosslink to form a solid crosslinked polymer structure, wherein the membrane isolates a vacuum of the vacuum chamber from vapor of the liquid composition in the sample chamber.

16 Claims, 14 Drawing Sheets

(51) Int. Cl.
| | |
|---|---|
| *B01D 67/00* | (2006.01) |
| *B29C 64/307* | (2017.01) |
| *B29C 64/245* | (2017.01) |
| *B33Y 40/00* | (2020.01) |
| *B29C 65/82* | (2006.01) |
| *B33Y 50/02* | (2015.01) |
| *B29C 64/40* | (2017.01) |
| *B33Y 99/00* | (2015.01) |
| *B29C 64/255* | (2017.01) |
| *B29C 64/30* | (2017.01) |
| *B22F 12/82* | (2021.01) |
| *B29C 64/10* | (2017.01) |
| *B29C 64/205* | (2017.01) |
| *B33Y 40/10* | (2020.01) |
| *H01J 37/32* | (2006.01) |
| *B22F 12/00* | (2021.01) |
| *B33Y 70/00* | (2020.01) |
| *B29C 64/182* | (2017.01) |
| *B29C 64/25* | (2017.01) |
| *G01N 23/2251* | (2018.01) |
| *B33Y 50/00* | (2015.01) |
| *B29C 64/386* | (2017.01) |
| *B29C 64/176* | (2017.01) |
| *B29C 64/227* | (2017.01) |
| *B22F 10/00* | (2021.01) |
| *B22F 10/85* | (2021.01) |
| *B29C 64/393* | (2017.01) |
| *B29C 64/20* | (2017.01) |
| *B33Y 30/00* | (2015.01) |
| *B33Y 80/00* | (2015.01) |
| *B33Y 40/20* | (2020.01) |
| *B33Y 10/00* | (2015.01) |
| *H01J 37/20* | (2006.01) |
| *G02B 21/34* | (2006.01) |
| *G01N 21/956* | (2006.01) |
| *G01N 33/50* | (2006.01) |

(52) U.S. Cl.
CPC ........ *B01D 67/00415* (2022.08); *B22F 10/00* (2021.01); *B22F 10/85* (2021.01); *B22F 12/00* (2021.01); *B22F 12/82* (2021.01); *B29C 64/00* (2017.08); *B29C 64/10* (2017.08); *B29C 64/176* (2017.08); *B29C 64/182* (2017.08); *B29C 64/20* (2017.08); *B29C 64/205* (2017.08); *B29C 64/227* (2017.08); *B29C 64/245* (2017.08); *B29C 64/25* (2017.08); *B29C 64/255* (2017.08); *B29C 64/30* (2017.08); *B29C 64/307* (2017.08); *B29C 64/386* (2017.08); *B29C 64/393* (2017.08); *B29C 64/40* (2017.08); *B29C 65/8253* (2013.01); *B29C 65/8292* (2013.01); *B33Y 40/00* (2014.12); *B33Y 40/10* (2020.01); *B33Y 50/00* (2014.12); *B33Y 50/02* (2014.12); *B33Y 70/00* (2014.12); *B33Y 99/00* (2014.12); *G01N 23/2251* (2013.01); *H01J 37/3244* (2013.01); *B01D 2323/30* (2013.01); *B33Y 10/00* (2014.12); *B33Y 30/00* (2014.12); *B33Y 40/20* (2020.01); *B33Y 80/00* (2014.12); *G01N 33/50* (2013.01); *G01N 2021/95676* (2013.01); *G01N 2223/418* (2013.01); *G02B 21/34* (2013.01); *G03G 2215/2054* (2013.01); *G05B 2219/49023* (2013.01); *G06T 2207/10061* (2013.01); *G06V 2201/122* (2022.01); *H01J 37/20* (2013.01); *H01J 2237/006* (2013.01); *H01J 2237/2003* (2013.01); *H01J 2237/2608* (2013.01); *Y10S 148/143* (2013.01); *Y10T 156/1722* (2015.01); *Y10T 156/1798* (2015.01)

(56) References Cited

U.S. PATENT DOCUMENTS

| | | |
|---|---|---|
| 2005/0008828 A1 | 1/2005 | Libera et al. |
| 2006/0014003 A1 | 1/2006 | Libera et al. |
| 2008/0274161 A1 | 11/2008 | Muratoglu et al. |
| 2011/0014436 A1 | 1/2011 | Stiles et al. |
| 2013/0146221 A1* | 6/2013 | Kolmakov ............... H01J 37/20 156/252 |
| 2016/0351374 A1* | 12/2016 | Wang ...................... C23F 1/40 |

OTHER PUBLICATIONS

Wang, J., et al., "Chemically selective soft X-ray patterning of polymers", Journal of Synchrotron Radiation, 2007, p. 181-190, vol. 14.

Sun, Y., et al., Chapters 11-22, Applications of Ionizing Radiation in Materials Processing, 2017, p. 249-516, vol. 2.

Ehrfeld, W., et al., "Deep X-ray Lithography for the Production of Three-Dimensional Microstructures from Metals, Polymers and Ceramics", Radiat. Phys. Chem., 1995, p. 349-365, vol. 45 No.3.

Bae, M., et al., "Fabrication of poly(ethylene glycol) hydrogel structures for pharmaceutical applications using electron beam and optical lithography" Journal of Vacuum Science and Technology B, 2010, p. C6P24-C6P29, vol. 28.

Esfandiarpour, S., et al., "Focused electron beam induced deposition of copper with high resolution and purity from aqueous solutions", Nanotechnology, 2017, p. 125301, vol. 28.

Meyerbroker, N., et al., "Modification and Patterning of Nanometer-Thin Poly(ethylene glycol) Films by Electron Irradiation", ACS Applied Materials & Interfaces, 2013, p. 5129-5138, vol. 5.

Fisher, J., et al., "Rapid Electron Beam Writing of Topologically Complex 3D Nanostructures Using Liquid Phase Precursor", Nano Letters, 2015, p. 8385-8391, vol. 15.

* cited by examiner

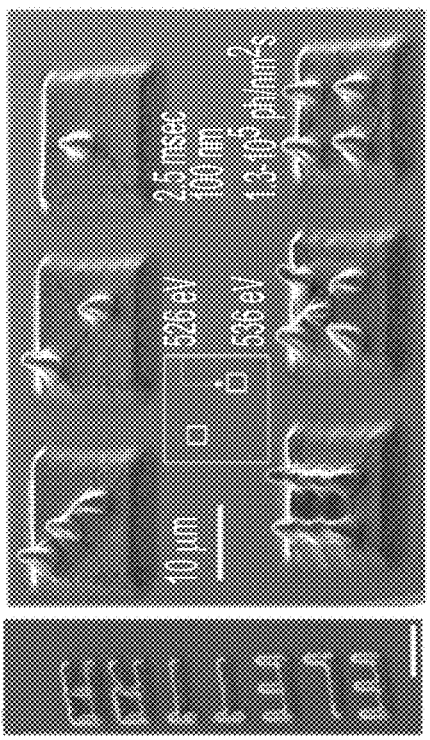
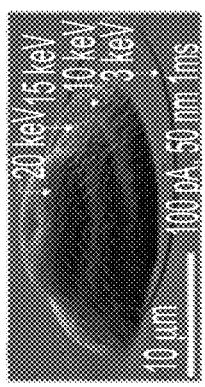
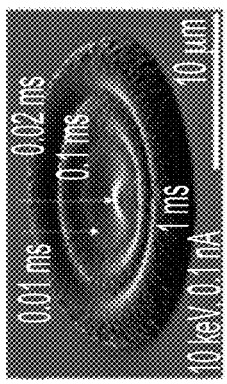
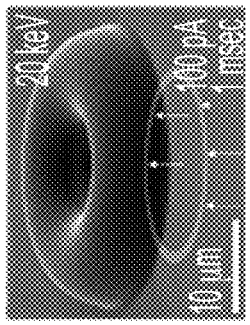
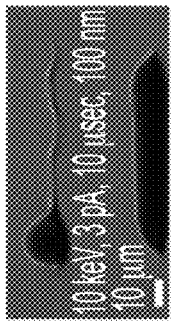
FIG. 10A FIG. 10B FIG. 10C FIG. 10D FIG. 10E FIG. 10F FIG. 10G

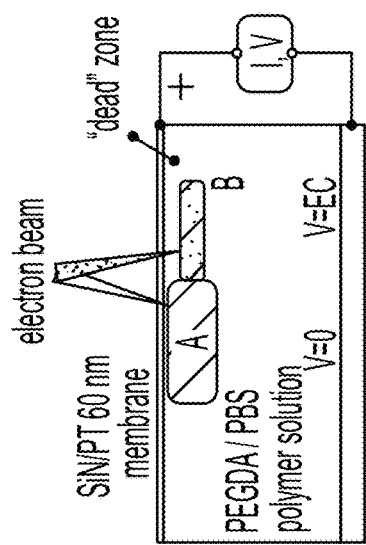
FIG. 11A
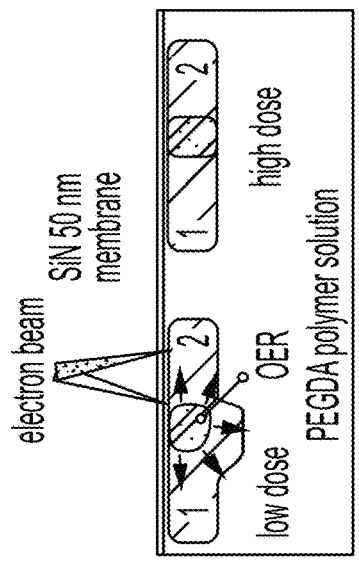
FIG. 11B
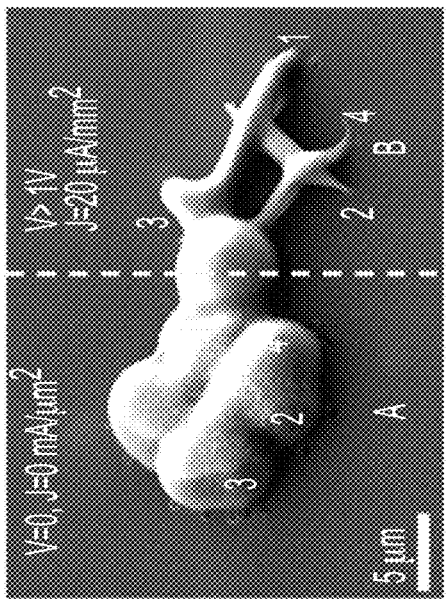
FIG. 11C
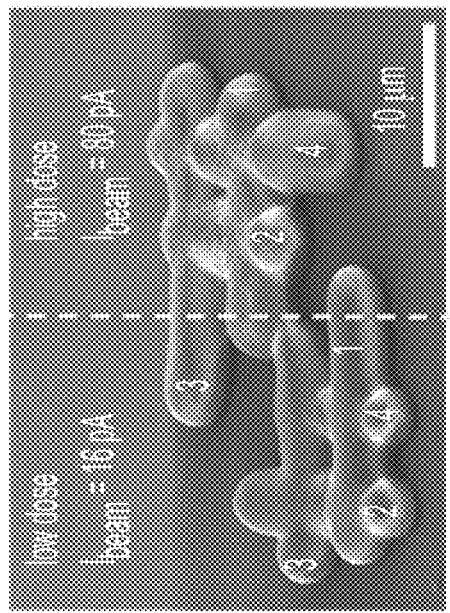
FIG. 11D
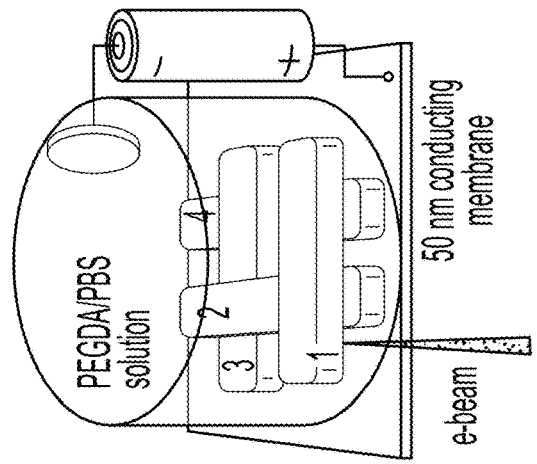

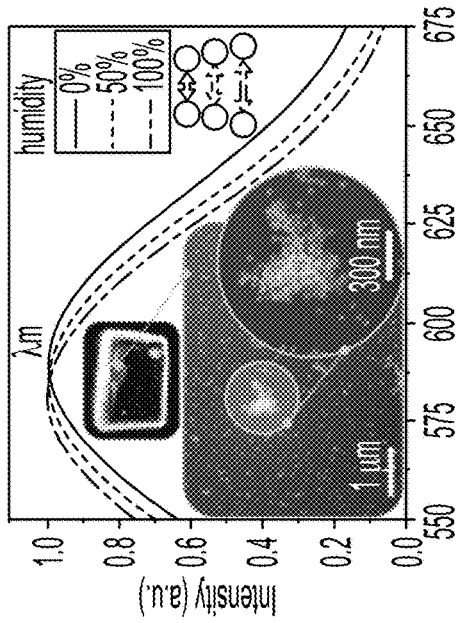
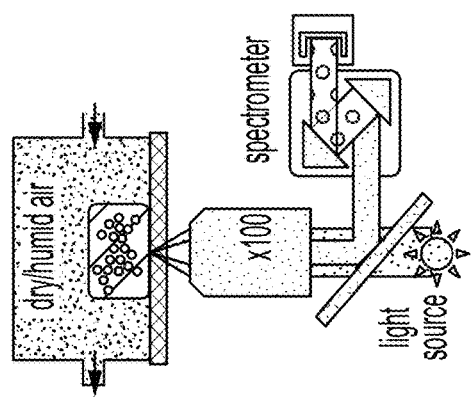
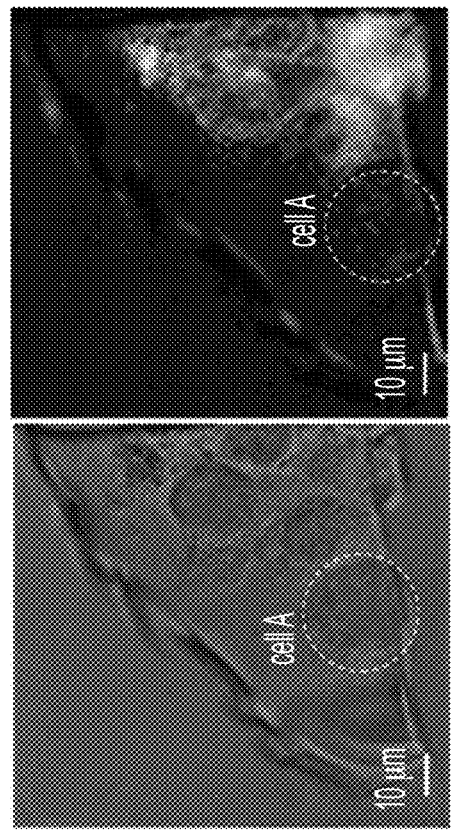
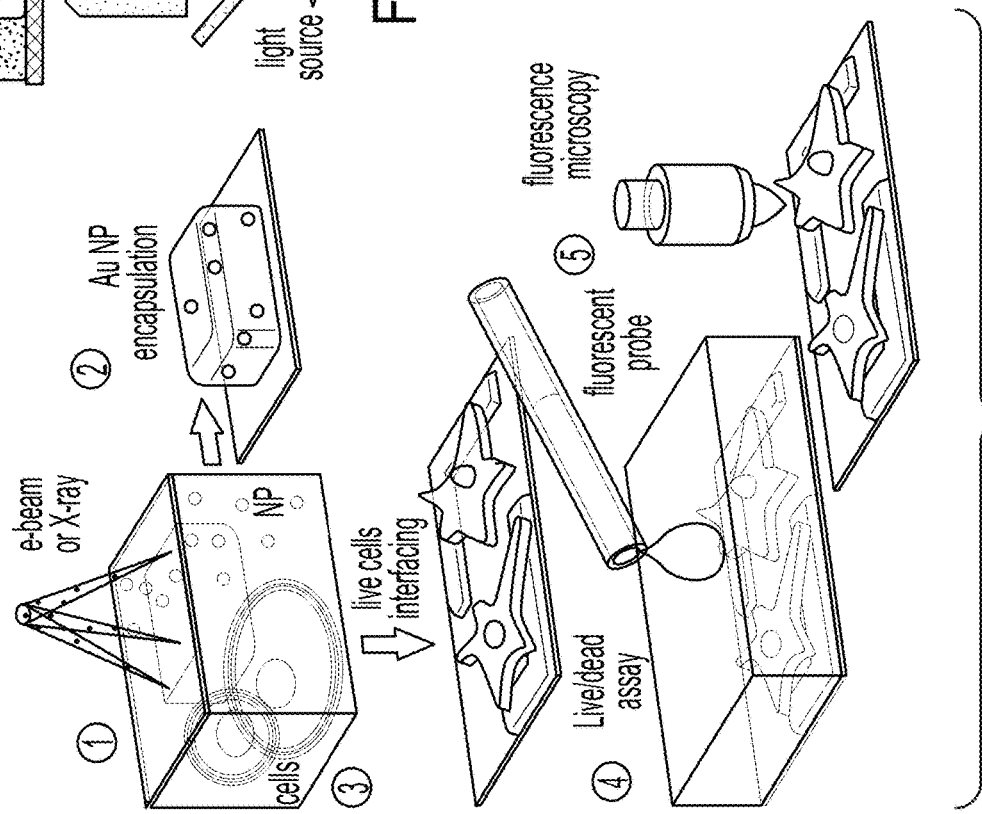
FIG. 12A
FIG. 12B
FIG. 12C
FIG. 12D
FIG. 12E

000
MULTIDIMENSIONAL PRINTER

CROSS REFERENCE TO RELATED APPLICATIONS

The application claims priority to U.S. Provisional Patent Application Ser. No. 62/881,667, filed Aug. 1, 2019, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce and The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 19-018US1.

BRIEF DESCRIPTION

Disclosed is a multidimensional printer for making a multidimensional structure from a liquid composition, the multidimensional printer comprising: an energetic crosslinking particle source that produces energetic crosslinking particles; a vacuum chamber in vacuum communication with the energetic crosslinking particle source and that receives the energetic crosslinking particles from the energetic crosslinking particle source and communicates the energetic crosslinking particles to a membrane; the membrane in particle communication with the vacuum chamber and comprising a barrier layer and a transmission layer disposed on the barrier layer, wherein a portion of the membrane has some of the transmission layer in an absence of the barrier layer for transmission of the energetic crosslinking particles through the transmission layer without being obstructed by the barrier layer, such that the membrane: receives the energetic crosslinking particles from the vacuum chamber; blocks, by the barrier layer, the energetic crosslinking particles from being further communicated in the multidimensional printer; and transmits, by the transmission layer, the energetic crosslinking particles for further communication in the multidimensional printer; and a sample chamber in communication with the membrane and that: receives a liquid composition that comprises a solvent and a plurality of polymers disposed in the solvent, the polymers comprising a cross-linkable moiety; receives the energetic crosslinking particles communicated from the transmission layer of the membrane; subjects the cross-linkable moieties of the polymers to the energetic crosslinking particles such that portions of the polymers proximate to the cross-linkable moieties subjected to the energetic crosslinking particles crosslink to form a solid crosslinked polymer structure, wherein the membrane isolates a vacuum of the vacuum chamber from vapor of the liquid composition in the sample chamber.

Disclosed is a process for making a multidimensional structure from a liquid composition with the multidimensional printer, the process comprising: disposing a liquid composition in the sample chamber; producing, by the energetic crosslinking particle source, the energetic crosslinking particles; receiving, by the vacuum chamber, the energetic crosslinking particles, from the energetic crosslinking particle source; communicating the energetic crosslinking particles from the vacuum chamber to the membrane; receiving, by the membrane, the energetic crosslinking particles from the vacuum chamber; transmitting, by the transmission layer of the membrane, the energetic crosslinking particles for communication to the sample chamber; receiving, by the liquid composition in the sample chamber, the energetic crosslinking particles from the membrane; subjecting the cross-linkable moieties of the polymers to the energetic crosslinking particles; crosslinking portions of the polymers proximate to the cross-linkable moieties subjected to the energetic crosslinking particles in response to receiving the energetic crosslinking particles; forming the solid crosslinked polymer structure in response to crosslinking the polymers to make the multidimensional structure.

BRIEF DESCRIPTION OF THE DRAWINGS

The following description should not be considered limiting in any way. With reference to the accompanying drawings, like elements are numbered alike.

FIG. 11 shows layer-by-layer beam writing of overlapping structures in liquid composition 201 that included PEGDA. Panel A shows sequential writing of overlapping structures. Panel B shows a model log-pile structure printed with and without anodic potential on a SiN/Pt electrode. Panel C shows morphology of the e-beam printed PEGDA structure depended on the writing sequence 1-2-3-4 for low-dose exposure and was independent for saturated crosslinking density; Panel D shows electrochemical size and adhesion control of in-liquid crosslinked structures for no electrochemical bias (V=0) applied and for applied cathodic potential V>1 volt and current density J=20 µA/mm$^2$, wherein reduction of feature size and footprint are shown as result of presence of energetic crosslinking particles; and FIG. 12 shows solid crosslinked polymer structure formed for applications of a multidimensional printer with e-beam and X-ray printing in liquid composition. Panel A shows e-beam induced encapsulation and interconnection of microobjects and nanoobjects using in liquid cured gel. Step (1) involves irradiation and in-liquid patterning of the nanoparticles or cells in a hydrogel precursor suspension through a SiN membrane followed by step (2) or step (3) for microscopic and spectroscopic characterization in a dry or wet stage. Step (4) involves hydrogel interfaced cells treated with a fluorescent probe for viability tests. Step (5) involves fluorescence microscopy of biological objects interfaced with a gel. Panel B shows excitation and recording of LSPR signal from e-beam printed Au NP/PEGDA composite hydrogel plasmonic sensor as a function of ambient humidity. Panel C shows normalized reflectance signal collected from PEGDA incapsulated 50 nm Au assembly as a function of the humidity. Insets show dark-field optical image of e-printed composite hydrogel pack and SEM images of Au NP assembly where signal was collected from. Panel D shows an optical microscopy image of hydrogel after electron beam irradiation of cell-laden PEGDA solution. Panel E shows a fluorescence microscopy image of gel interfaced cells stained with viability indicator such as alcein green dye, wherein a dashed line indicates a necrotic cell.

DETAILED DESCRIPTION

Figure 1:
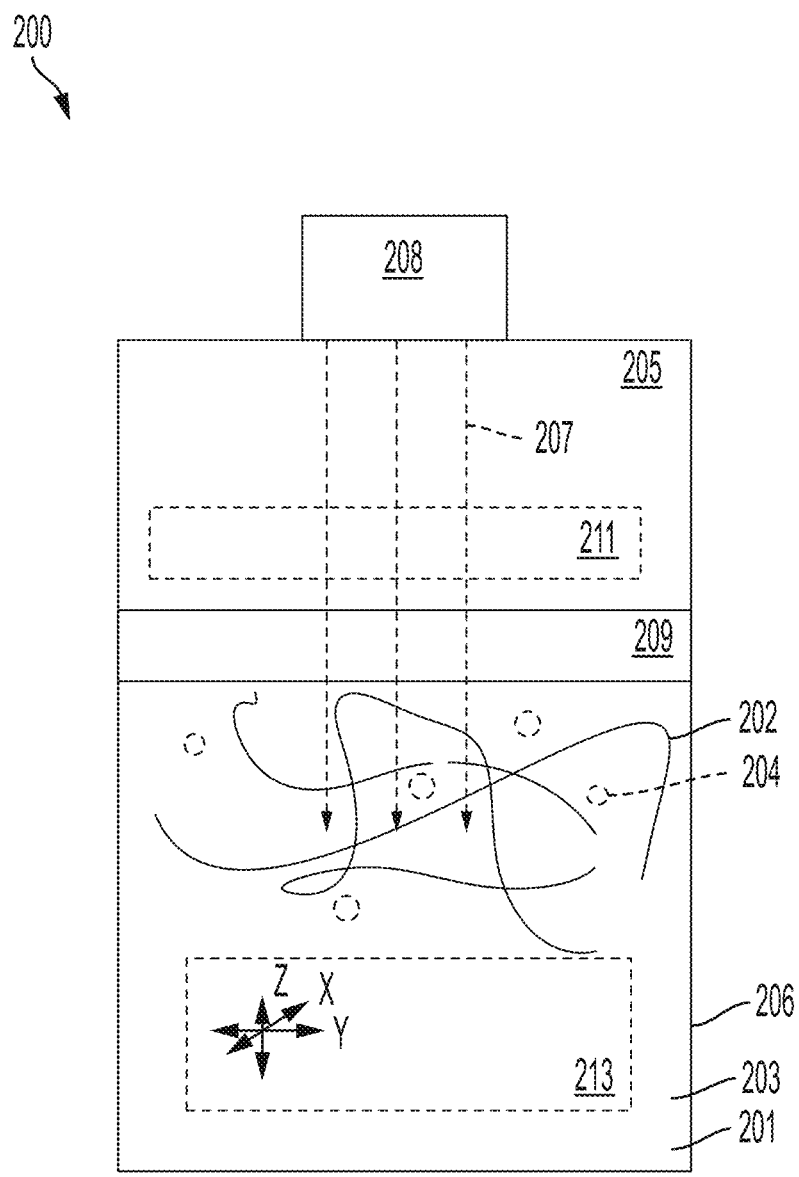
FIG. 1 shows a multidimensional printer for making a solid crosslinked polymer structure.

A detailed description of one or more embodiments is presented herein by way of exemplification and not limitation.

It has been discovered a multidimensional printer and process for printing described herein provide patterning of hydrogels in a native, liquid state by electrons or x-rays respectively transmitted through an electron or x-ray transparent membrane. The membrane can be molecularly impermeable or partially molecularly permeable and separates electron optics or x-ray optics from a pressure of gas from a liquid sample. Dependence of an attenuation length of electrons and x-ray radiation in a condensed medium on energy controls crosslinking of a polymer in a liquid composition to make two-dimensional and three-dimensional gel structures, referred to as a solid crosslinked polymer structure, with submicron spatial resolution. An advantage of such compared to conventional dry gel patterning includes micropatterning of the liquid composition in a liquid state and additive fabrication of multi-compositional two-dimensional and three-dimensional solid crosslinked polymer structures as gel constructs, e.g., for tissue or soft robotics engineering; addressable gel-encapsulation of an object, e.g., a drug, biomolecule, functional nanoparticle, and the like; or gel-coating or patterning of functional entities such as a live biological object, composite, electrochemical electrode, and the like.

Beneficially, the multidimensional printer herein provides fabrication of two-dimensional and three-dimensional 3D structures out of liquid biocompatible hydrogel solutions (the liquid composition) for tissue engineering, soft robotics, biosensing, drug delivery, wound treatment, or other biomedical research.

Conventional additive manufacturing from liquid gels is based on photoinduced crosslinking of the polymer solution and can be limited to micron-level spatial resolution by a diffraction limit of photon optics. The multidimensional printer overcomes this limitation and includes electrons or X-rays as energetic crosslinking particles to initiate crosslinking with smaller wavelength and mean free path in condensed phase matter, wherein the energetic crosslinking particles can be controlled by their energy. In an absence of multidimensional printer 200 and just using e-beam lithography or X-ray lithography, one obtains a two-dimensional lithography process that requires vacuum conditions and dry samples, i.e., operation in an absence of a target (e.g., a cross-linkable polymer) disposed in a liquid and lacks three-dimensional printing in a continuous process. The multidimensional printer 200 herein overcomes this technical limitation and includes the electron or X-ray transparent membrane to isolate a vacuum of a radiation source chamber source the liquid chamber.

In the multidimensional printer, the electron or X-ray beam penetrates into the liquid after passing through the membrane and crosslinks the polymers in the liquid composition within an interaction volume. The spatial resolution of the multidimensional printer can depend on a size of the interaction volume, which can be a function of electron or X-ray energy that can be tuned, e.g., from 10 nm to tens of microns. In addition, a structural size or degree of crosslinking can be controlled by an irradiation dose (e.g., flux, exposure time, dwell time, pitch size in case of scanning), temperature (e.g., diffusion), or concentration of polymer, or inclusion of a solute.

Figure 2:
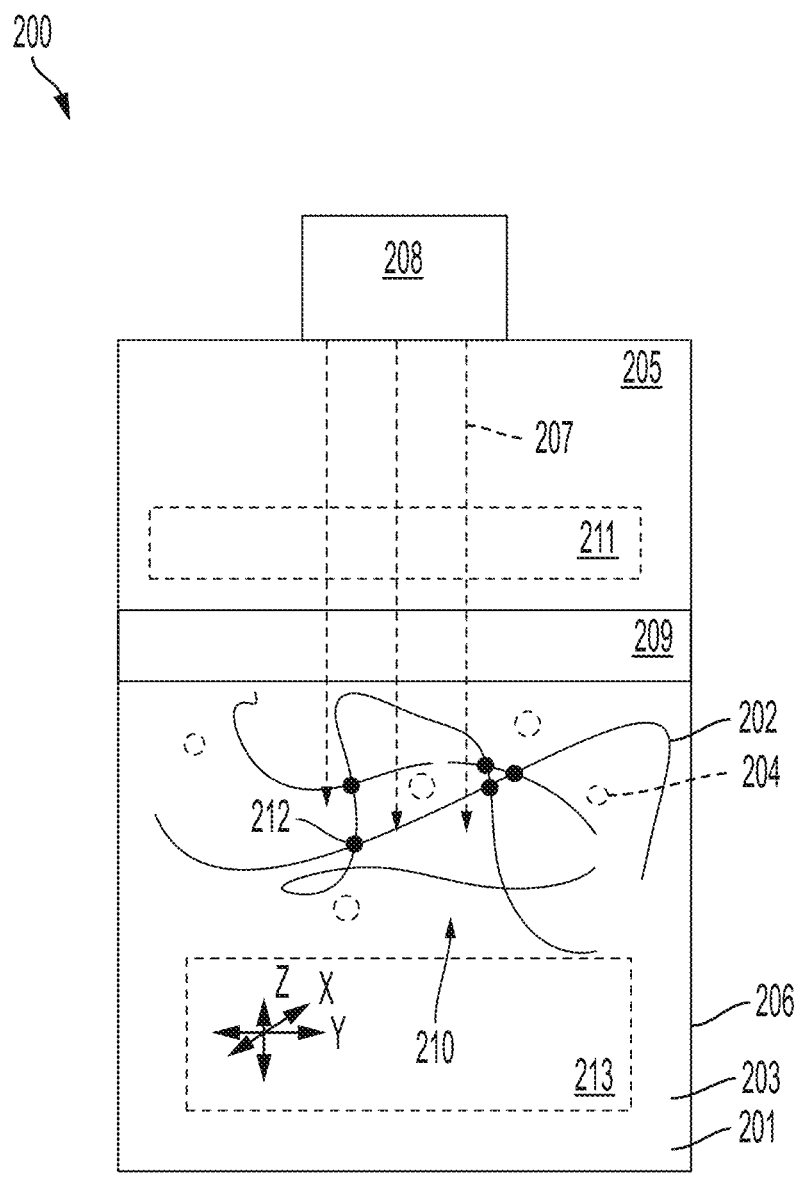
FIG. 2 shows a multidimensional printer with crosslinks in a solid crosslinked polymer structure.
Figure 3A:
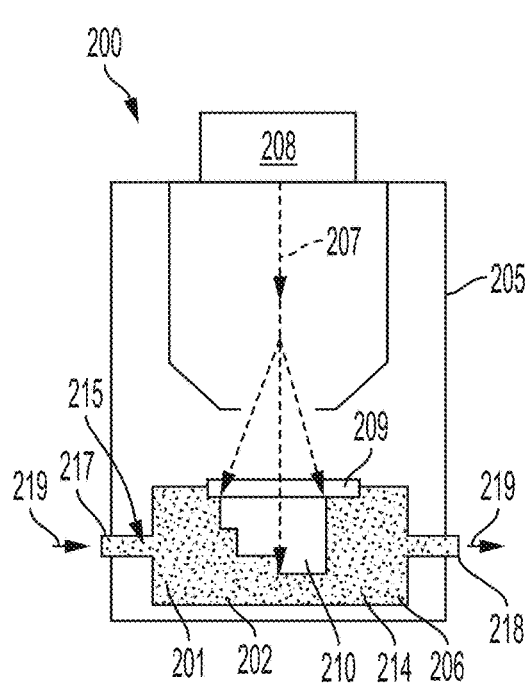
FIG. 3 shows a plurality of configurations for a multidimensional printer in panels A, B, C, and D.
Figure 3B:
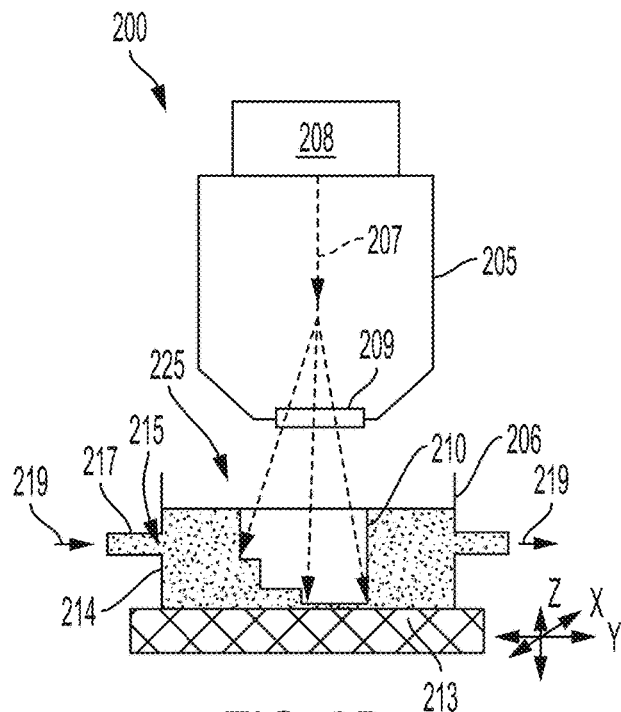
Figure 3C:
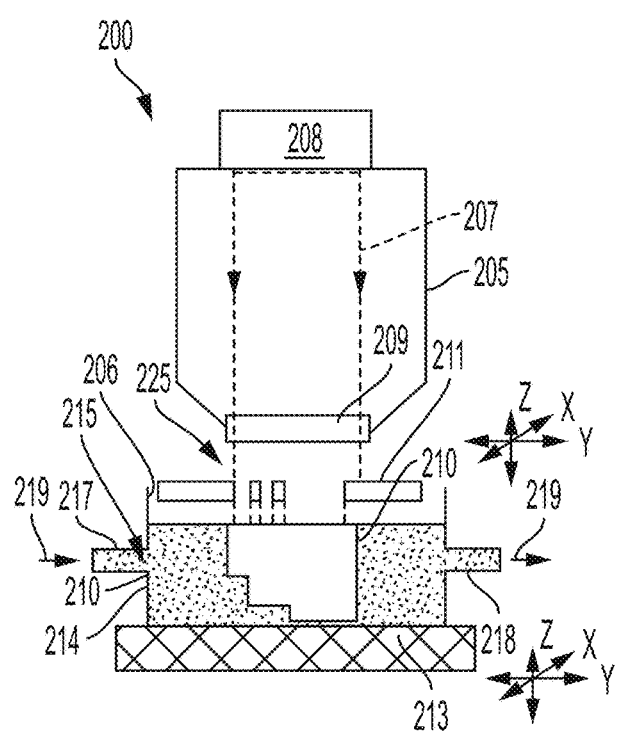
Figure 3D:
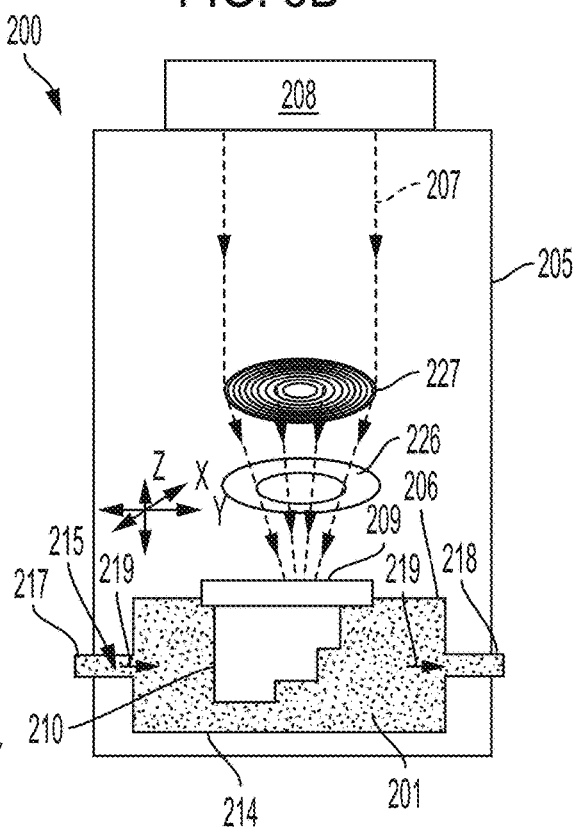

Multidimensional printer 200 makes a multidimensional structure from a liquid composition. In an embodiment, with reference to FIG. 1, FIG. 2, and FIG. 3, multidimensional printer 200 includes: energetic crosslinking particle source 208 that produces energetic crosslinking particles 207; vacuum chamber 205 in vacuum communication with energetic crosslinking particle source 208 and that receives energetic crosslinking particles 207 from energetic crosslinking particle source 208 and communicates energetic crosslinking particles 207 to membrane 209; membrane 209 in particle communication with vacuum chamber 205 and including barrier layer 228 and transmission layer 229 disposed on barrier layer 228, wherein a portion of membrane 209 has some of transmission layer 229 in an absence of barrier layer 228 for transmission of energetic crosslinking particles 207 through transmission layer 229 without being obstructed by barrier layer 228, such that membrane 209: receives energetic crosslinking particles 207 from vacuum chamber 205; blocks, by barrier layer 228, energetic crosslinking particles 207 from being further communicated in multidimensional printer 200; and transmits, by transmission layer 229, energetic crosslinking particles 207 for further communication in multidimensional printer 200; and sample chamber 206 in communication with membrane 209 and that: receives liquid composition 201 that includes solvent 203 and a plurality of polymers 202 disposed in solvent 203, polymers 202 including a cross-linkable moiety; receives energetic crosslinking particles 207 communicated from transmission layer 229 of membrane 209; subjects the cross-linkable moieties of polymers 202 to energetic crosslinking particles 207 such that portions of polymers 202 proximate to the cross-linkable moieties subjected to energetic crosslinking particles 207 crosslink to form solid crosslinked polymer structure 210, wherein membrane 209 isolates a vacuum of vacuum chamber 205 from vapor of liquid composition 201 in sample chamber 206.

With reference to FIG. 3, multidimensional printer 200 can be configured in various ways, wherein membrane 209 seals sample chamber 206 that can, e.g., be disposed in vacuum chamber 205 of an electron microscope as shown in panel A of FIG. 3. An output optical element of the microscope can be capped with membrane 209 and liquid composition 201 with free liquid surface being under ambient conditions as shown in panels B and C in FIG. 3. Lateral resolution for crosslinking polymers 202 in liquid composition 201 by energetic crosslinking particles 207 can be provided by electron optics or X-ray optics disposed in energetic crosslinking particle source 208 or vacuum chamber 205 to provide focused radiation as shown in panels A and B in FIG. 3 or by placement of shadow mask 211 as shown in panel C of FIG. 3 for unfocused radiation. In some embodiments, zone plate 227 and order sorting aperture 226 can be interposed between energetic crosslinking particle source 208 and membrane 209 for controlling a beam profile of energetic crosslinking particles 207 received by liquid composition 201 as shown in panel D of FIG. 3. Further, two-dimensional patterning of solid crosslinked polymer structure 210 can be achieved via rastering of the focused beam of energetic crosslinking particles 207 or solid crosslinked polymer structure 210 via their relative motion or via X-positioning or Y-positioning of shadow mask 211 relative to liquid composition 201 for unfocused energetic crosslinking particles 207.

Three-dimensional features in solid crosslinked polymer structure 210 can be formed by aforementioned two-dimensional positioning with either modulation of the energy and intensity of energetic crosslinking particles 207 or additively replenishing a liquid layer of liquid composition 201 in contact with solid crosslinked polymer structure 210 such that the polymers 202 in the replenished liquid layer is subject to crosslinking added polymers to existing solid crosslinked polymer structure 210.

Energetic crosslinking particle source 208 produces energetic crosslinking particles 207. Energetic crosslinking particles 207 includes electrons or X-rays. Energetic crosslinking particle source 208 can include elements that focus, modulate, or energy-select energetic crosslinking particles 207 such that energetic crosslinking particles 207 can be formed in a beam that is continuous or modulated. Further, energetic crosslinking particles 207 can be focused (e.g., in a focused beam of energetic crosslinking particles 207, or diffuse, such as in a flood beam of energetic crosslinking particles 207. Exemplary energetic crosslinking particle source 208 that provide electrons as energetic crosslinking particles 207 includes an electron gun, filament, cathode, electron microscope, and the like. Exemplary energetic crosslinking particle source 208 that provide X-rays as energetic crosslinking particles 207 includes an X-ray tube and the like. An energy of energetic crosslinking particles 207 can be from 10 eV to 1000 keV, specifically from 1 keV to 30 keV, and specifically from 1 keV to 10 keV. A type of energetic crosslinking particles 207 can be electrons, hard UV photons, X-ray photons or ions. In an embodiment, energetic crosslinking particles 207 includes gamma rays.

Vacuum chamber 205 provides a vacuum environment for energetic crosslinking particle source 208 and a propagation medium through which energetic crosslinking particles 207 propagate from energetic crosslinking particle source 208 to membrane 209. A pressure of vacuum chamber 205 can be selected to provide a mean free path or energy filtering of energetic crosslinking particles 207. It is contemplated that the pressure of vacuum chamber 205 can be from $10^{-10}$ Pa to 1 Pa, specifically from $10^{-4}$ Pa to $10^{-1}$ Pa, and more specifically from $10^{-3}$ to $10^{-2}$ Pa.

Figure 6A:
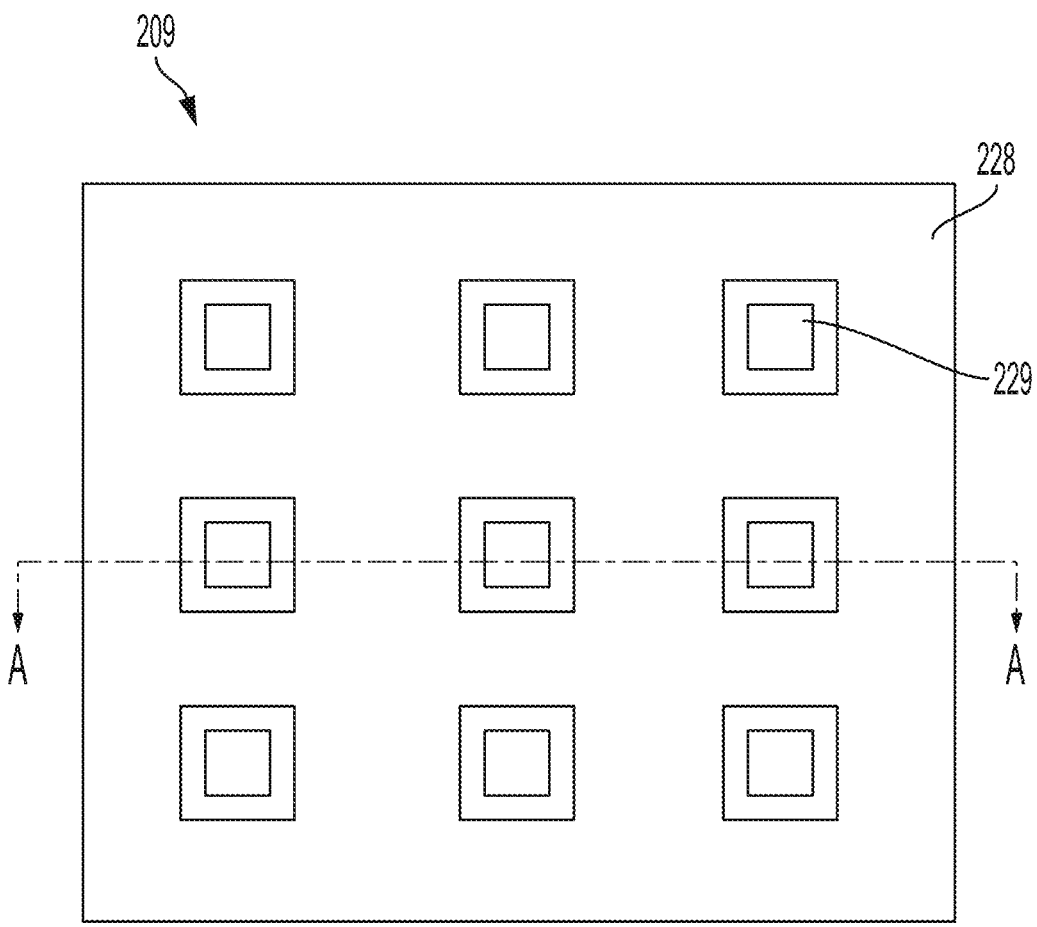
FIG. 6 shows a plan view of a membrane in panel A and, in panel B, a cross-section along line A-A of the membrane.
Figure 6B:
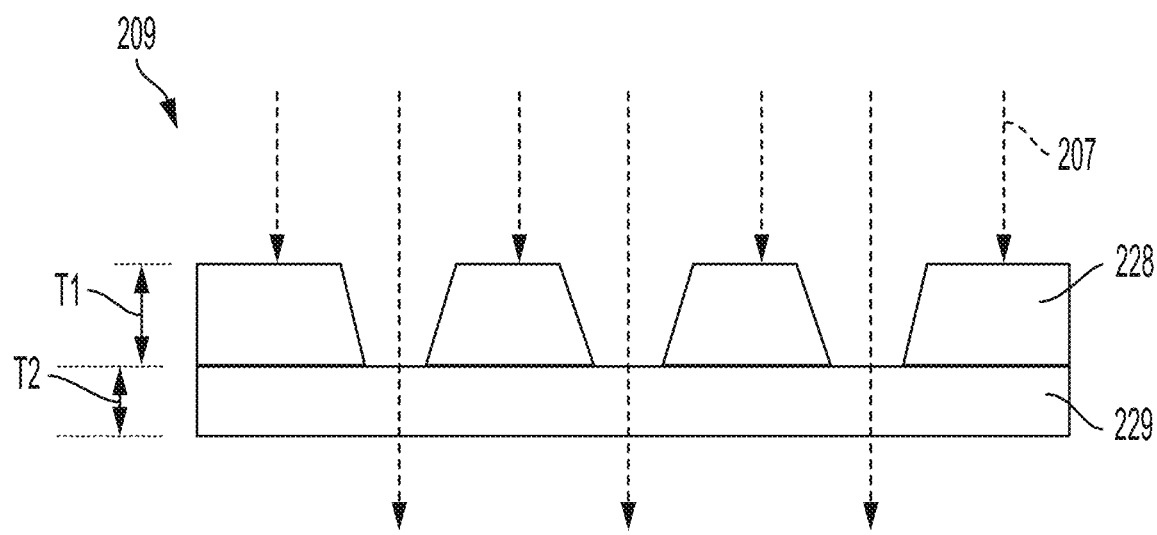

In an embodiment, with additional reference to FIG. 6, membrane 209 includes barrier layer 228 and transmission layer 229 disposed on barrier layer 228. Barrier layer 228 can include a material that attenuates an intensity of energetic crosslinking particles 207 transmitted through barrier layer 228. The attenuation efficiency can be partial or complete, i.e., 100%. Attenuation includes absorption or redirection of a trajectory of energetic crosslinking particles 207 such as refraction or reflection. Membrane 209 can be made of any material such as a low-Z material with a thickness that is less than electron or X-ray inelastic mean free path in such material at an energy of printing and having mechanical strength that withstands a pressure differential between sample chamber 206 and vacuum chamber 205. Exemplary barrier layers 228 include a material that attenuate electron transmission such as silicon, material that attenuates X-ray transmission such as silicon, or a combination thereof.

Transmission layer 229 can include a material that transmits energetic crosslinking particles 207. The transmission efficiency of transmission layer 229 can be partial or complete, i.e., 100%. Exemplary transmission layers 229 include a material that transmits electrons such as silicon nitride, material that transmits X-rays such as silicon nitride, or a combination thereof. First thickness T1 of barrier layer 228 can be from 10 nm to $10^4$ nm, specifically from 100 nm to 1000 nm. Second thickness T2 of transmission layer 229 can be from 0.34 nm to 1000 nm, specifically from 5 nm to 100 nm, and more specifically from 10 nm to 30 nm. Further, barrier layer 228 can include a plurality of apertures in a select pattern over which or in which is disposed transmission layer 229. In this manner, membrane 209 isolates gas from leaving sample chamber 206 and entering vacuum chamber 205 and spatially selects energetic crosslinking particles 207 from vacuum chamber 205 being transmitted to liquid composition 201 through transmission layer 229.

Figure 7A:
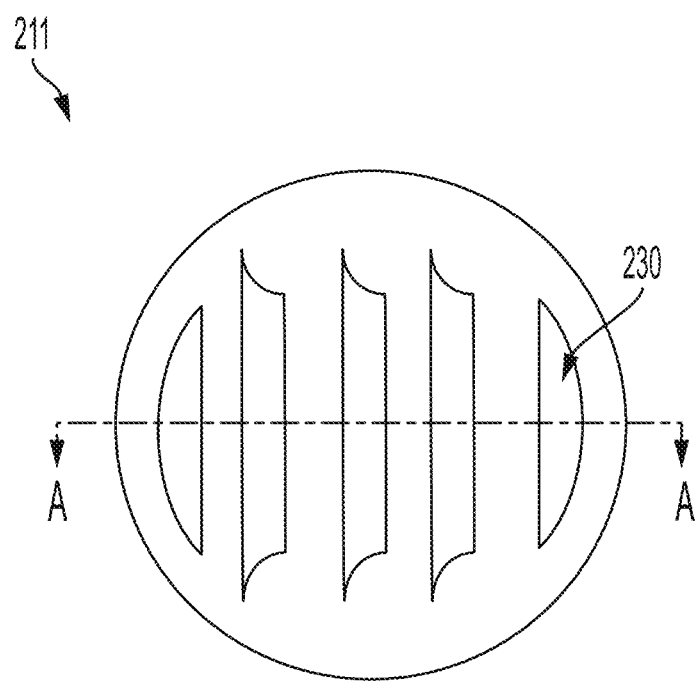
FIG. 7 shows a plan view of a shadow mask in panel A and, in panel B, a cross-section along line A-A of the shadow mask.
Figure 7B:
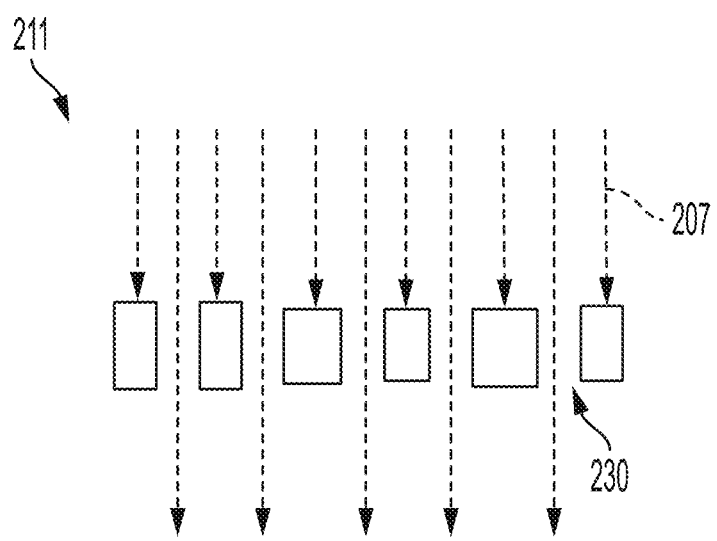

In an embodiment, with additional reference to FIG. 7, multidimensional printer 200 further includes shadow mask 211 interposed between energetic crosslinking particle source 208 and membrane 209 and that receives energetic crosslinking particles 207 from energetic crosslinking particle source 208 and communicates energetic crosslinking particles 207 to membrane 209, wherein shadow mask 211 selectively controls transmission of energetic crosslinking particles 207 through shadow mask 211 via apertures 230 disposed in shadow mask 211. Shadow mask 211 includes a plurality of aperture 230 that transmits energetic crosslinking particles 207. The transmission efficiency of aperture 230 can be partial or complete. Exemplary shadow masks include metals, plastics, ceramic, and the like. Further, aperture 230 can be disposed in shadow mask 211 in a select pattern and can have an arbitrary cross-sectional shape (e.g., polygonal, round) and size that can be used to limit a flux of energetic crosslinking particles 207 or form a particular cross-sectional shape of energetic crosslinking particles 207.

Figure 4:
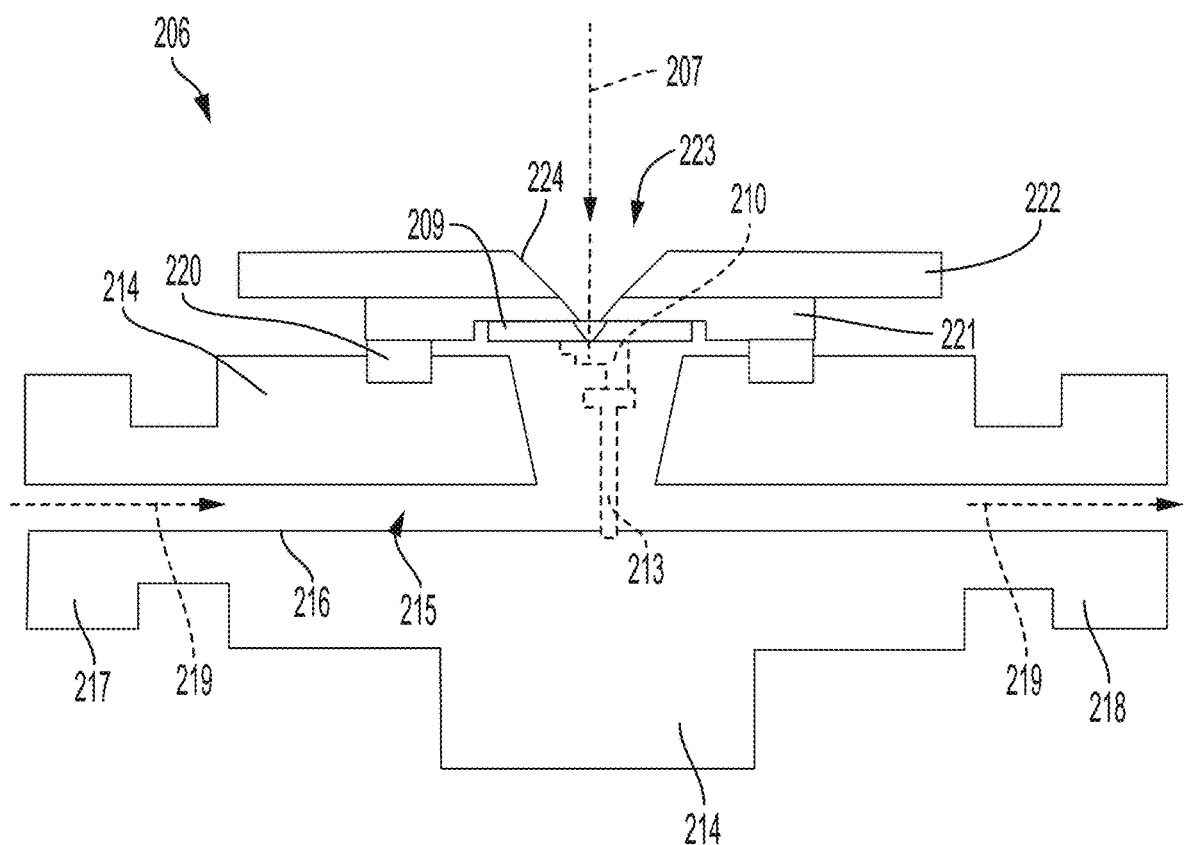
FIG. 4 shows a cross-section of a sample chamber.

In an embodiment, with additional reference to FIG. 4, multidimensional printer 200 further includes sample translation stage 213 disposed in sample chamber 206 and in mechanical communication with solid crosslinked polymer structure 210 produced from crosslinking polymers 202 by energetic crosslinking particles 207, wherein sample translation stage 213 translates away from membrane 209, toward membrane 209, or laterally with respect to membrane 209 so that a two-dimensional or three-dimensional size or shape of solid crosslinked polymer structure 210 can be spatially controlled during formation of solid crosslinked polymer structure 210 from polymers 202. Exemplary translation stages 213 includes a piezoelectric stage and the like. A step size of sample translation stage 213 can be from 1 nm to $10^4$ nm, specifically from 10 nm to 1000 nm, Further, sample translation stage 213 can perform X, Y, Z independent movements with aforementioned step sizes as well rotation from and tilt from 0° to 360° with precision from 0.001 rad to 1 rad.

Sample chamber 206 receives energetic crosslinking particles 207 from membrane 209 and also receives liquid composition 201 for interaction with energetic crosslinking particles 207. Sample chamber 206 can provide a static volume of liquid composition 201 or can include elements for flowing liquid composition 201 through sample chamber 206. Accordingly, during formation of solid crosslinked polymer structure 210, liquid composition 201 in sample chamber 206 is a static liquid volume or is subject to fluid flow through sample chamber 206. In an embodiment, with reference to FIG. 4 and FIG. 5, sample chamber 206 includes flow chamber 214; flow channel 215 bounded by wall 216 of flow chamber 214; inlet port 217 that receives liquid composition 201 for fluid communication through flow channel 215 in a direction of fluid flow 219; outlet port 218 for outflow of liquid composition 201 from sample chamber 206; gasket 220 received in a gland embossed on a surface of flow chamber 214 to seal flow chamber 214 against membrane support 221 that receives membrane 209; and chamber lid 222 in mechanical communication with membrane support 221 and flow chamber 214 and that is fastened to flow chamber 214 to maintain force on membrane support 221 and gasket 220. Elements of sample chamber 206 can include a material compatible with liquid composition 201 and energetic crosslinking particles 207. Exemplary materials include metals, plastics, glass, and the like. A flow rate of liquid composition 201 through flow channel 215 can be from 0 μL/sec to 100 mL/s, specifically from 0 μL/sec to 100 μL/sec, and more specifically from 0 μL/sec to 10 μL/sec. A volume of flow channel 215 proximate to membrane 209 can be from 0.01 μL to 1 L, specifically from 0.1 0 μL to 100 0 μL, and more specifically from 1 0 μL to 10 μL. It is contemplated that a temperature of liquid composition 201 in sample chamber 206 can be controlled at an arbitrary temperature or allowed to obtain a temperature of liquid composition 201 entering inlet port 217. Additionally, motion and position of solid crosslinked polymer structure 210 formed in sample chamber 206 proximate to membrane 209 in flow channel 215 can be controlled by sample translation stage 213 disposed in sample chamber 206. Sample translation stage 213 can have electrical connections to external control electronics that provide electrical power for manipulation of the position of movement of sample translation stage 213 relative to membrane 209.

In an embodiment, sample chamber 206, membrane 209 includes a silicon chip with nine SiN 50 nm thin membranes disposed on the silicon chip and sealing the volume of flow channel 215 filled with liquid composition 201 that includes a PEGDA water solution. In this configuration, printing of solid crosslinked polymer structure 210 from liquid composition 201 was performed inside a scanning electron microscope (SEM) with beam energies of energetic crosslinking particles 207 from 3 keV to 30 keV via rastering focused electron beam with pre-programmed pitch size and dwell time.

Liquid hydrogel composition 201 includes polymers 202 and can be a static liquid volume or fluidic (e.g., microfluidic, exchangeable). It is contemplated that a portion of liquid composition 201 that is exposed to and receives energetic crosslinking particles 207 can be part of a system such as lab-on-a-chip or organ-on-a-chip with crosslinking polymers 202 being a part of processing with such system. Polymers 202 can be a single species or a plurality of species. Some of the species include cross-linkable moieties that can include a multiple bond such as a double bond or triple bond. Polymers 202 can be selected based on an application of solid crosslinked polymer structure 210. In an embodiment, polymer 202 includes poly(ethylene glycol) diacrylate that crosslinks via double bonds with initiation of crosslinking by interaction with energetic crosslinking particles 207. Polymer 202 can include a block polymer, copolymer, and the like. A molecular weight of polymer 202 can be from 100 Da to $10^6$ Da, specifically from 100 Da to $10^4$ Da, and more specifically from 100 Da to $10^3$ Da. Polymers 202 can be monodisperse or polydisperse.

In an embodiment, solvent 203 of liquid composition 201 is selected to solvate polymers 202. Exemplary solvents 203 include water, alcohols, phenylenediamines, ethylene carbonate, sulfuric acid, benzene, halogenated hydrocarbons, methyl ethyl ketone, hydrocarbons, esters, phenol, chlorophenol, phenol, dioxane, biphenyl, phenyl ether, xylene, 1,2-dichlorobenzene, toluene, chloroform, methanol, cyclohexanone, ethylene carbonate, and the like or combination thereof. In an embodiment, solvent 203 is water.

Solute 204 can be disposed in liquid composition 201 to receive energetic crosslinking particles 207 and cause localized crosslinking among polymers 202 proximate to solute 204. Exemplary solute 204 includes quantum dots, nanoparticles, or a combination comprising at least one of the foregoing solutes.

In according with the foregoing, a spatial resolution of forming solid crosslinked polymer structure 210 depends on a size of an interaction volume between polymers 202 and energetic crosslinking particles 207 and energy of energetic crosslinking particles 207. In this respect, the spatial resolution is tunable and is from 10 nm to 90 μm, specifically from 20 nm to 1000 nm, and more specifically from 50 nm to 100 nm. To achieve a selected geometrical shape or size, liquid composition 201 is subjected to relative rastering of energetic crosslinking particles 207 in liquid composition 201 for two-dimensional patterning of polymers 202 to form solid crosslinked polymer structure 210 having a selected two-dimensional pattern. The two-dimensional pattern can be arbitrary. Exemplary two-dimensional patterns include linear interconnects, closed structures, arbitrary geometrical shapes, and the like. It is contemplated that liquid composition 201, in contact with solid crosslinked polymer structure 210 having the selected two-dimensional pattern, can be subjected to modulation of an energy or intensity of energetic crosslinking particles 207 in liquid composition 201 such that addition of polymers 202 to solid crosslinked polymer structure 210 provide a selected three-dimensional geometry to solid crosslinked polymer structure 210 with the two-dimensional pattern. The two-dimensional pattern can be arbitrary. Exemplary two-dimensional patterns include linear interconnects, circular structures, geometrical figures of arbitrary shapes, and the like. In some embodiments, liquid composition 201, in contact with solid crosslinked polymer structure 210 having the selected two-dimensional pattern, receives additional polymers for crosslinking in presence of energetic crosslinking particles 207 such that additional polymers 202 are crosslinked to solid crosslinked polymer structure 210 to provide a selected three-dimensional geometry to solid crosslinked polymer structure 210 with the two-dimensional pattern.

Multidimensional printer 200 can be made in various ways. In an embodiment, a process for making multidimensional printer 200 includes filling the sample chamber 206 with printing solution, disposing energetic crosslinking particle source 208 on vacuum chamber 205; optionally disposing shadow mask 211 in vacuum chamber 205; disposing vacuum chamber 205 in communication with membrane 209; disposing sample chamber 206 in communication with membrane 209; disposing liquid composition 201 in sample chamber 206; and optionally disposing sample translation stage 213 in sample chamber 206 and in communication with sample chamber 206.

It will be appreciated that in making multidimensional printer 200 elements thereof are arranged components to be in communication so that energetic crosslinking particles 207 propagates from vacuum chamber 205 and received by liquid composition 201 in sample chamber 206 with vapor isolation of vacuum chamber 205 and sample chamber 206 by membrane 209 and arranging electrical components to communicate electrical signals amongst the various electrical components. Fluid flow and stoppage of liquid composition 201 in sample chamber 206 can occur via a fluid pump or like device.

The process for making multidimensional printer 200 also can include filling chamber 206 with precursor solution with or without solute inclusions solute 204; printing the layer via radiation induced crosslinking; activating delamination agent (electrochemical, electrophoretic, mechanical, capillary, thermal, photoinduced or their combination) to detach the print from the membrane if working without free liquid-gas interface; moving the stage and replenishing a liquid interface; repeating the printing of the next layer; and removing the sample from the solution upon completion Multidimensional printer 200 has numerous advantageous and unexpected benefits and uses. In an embodiment, a process for making a multidimensional structure from a liquid composition with multidimensional printer 200 includes: disposing liquid composition 201 in sample chamber 206; producing, by energetic crosslinking particle source 208, energetic crosslinking particles 207; receiving, by vacuum chamber 205, energetic crosslinking particles 207, from energetic crosslinking particle source 208; communicating energetic crosslinking particles 207 from vacuum chamber 205 to membrane 209; receiving, by membrane 209, energetic crosslinking particles 207 from vacuum chamber 205; transmitting, by transmission layer 229 of membrane 209, energetic crosslinking particles 207 for communication to sample chamber 206; receiving, by liquid composition 201 in sample chamber 206, energetic crosslinking particles 207 from membrane 209; subjecting the cross-linkable moieties of polymers 202 to energetic crosslinking particles 207; crosslinking portions of polymers 202 proximate to the cross-linkable moieties subjected to energetic crosslinking particles 207 in response to receiving energetic crosslinking particles 207; and forming solid crosslinked polymer structure 210 in response to crosslinking polymers 202 to make the multidimensional structure.

In an embodiment, the process for making a multidimensional structure from a liquid composition with multidimensional printer 200 further includes: receiving, by shadow mask 211 interposed between energetic crosslinking particle source 208 and membrane 209, energetic crosslinking particles 207 from energetic crosslinking particle source 208; communicating, energetic crosslinking particles 207 to membrane 209 from shadow mask 211; and selectively controlling transmission, by shadow mask 211, energetic crosslinking particles 207 through shadow mask 211 via apertures 230 disposed in shadow mask 211. Shadow mask 211 can be moved relative to solid crosslinked polymer structure 210 to control formation of crosslinks and resulting shape or size of solid crosslinked polymer structure 210.

In an embodiment, the process for making a multidimensional structure from a liquid composition with multidimensional printer 200 further includes spatially controlling, during formation of the solid crosslinked polymer structure 210 from the polymers 202, a two-dimensional or three-dimensional size or shape of the solid crosslinked polymer structure 210 by translating away from the membrane 209, toward the membrane 209, or laterally with respect to the membrane 209 the growing solid crosslinked polymer structure 210. Such motion can be provided by sample translation stage 213.

In an embodiment, the process for making a multidimensional structure from a liquid composition with multidimensional printer 200 further includes two-dimensional patterning of polymers 202 by subjecting liquid composition 201 to relative rastering of energetic crosslinking particles 207 in liquid composition 201 to form solid crosslinked polymer structure 210 having a selected two-dimensional pattern. Relative rastering can occur by rastering the radiation beam, shadow mask 211, sample stage 213 or their combination.

In an embodiment, the process for making a multidimensional structure from a liquid composition with multidimensional printer 200 further includes: subjecting liquid composition 201 in contact with solid crosslinked polymer structure 210 having the selected two-dimensional pattern to modulation of an energy or intensity of energetic crosslinking particles 207 in liquid composition 201; adding polymers 202 to solid crosslinked polymer structure 210 by crosslinking in response to subjecting liquid composition 201 to the modulation; and providing a selected three-dimensional geometry to solid crosslinked polymer structure 210 with the two-dimensional pattern in response to adding polymers 202 to solid crosslinked polymer structure 210.

In an embodiment, the process for making a multidimensional structure from a liquid composition with multidimensional printer 200 further includes: receiving, by liquid composition 201 in contact with solid crosslinked polymer structure 210 having the selected two-dimensional pattern, additional polymers; crosslinking the additional polymers to solid crosslinked polymer structure 210 by energetic crosslinking particles 207; and forming a selected three-dimensional geometry of solid crosslinked polymer structure 210 with two-dimensional pattern in response to crosslinking the additional polymers to solid crosslinked polymer structure 210.

Multidimensional printer 200 and processes disclosed herein have numerous beneficial, including higher spatial resolution, fast printing rate, and absence of chemical initiators. Advantageously, multidimensional printer 200 overcomes limitations of technical deficiencies of conventional compositions such as using crosslink initiators for two-photon crosslinking. Further, fine features as small as few tens of nanometers can be printed.

Conventional photo-induced three-dimensional printing exhibits resolution of order of hundreds of micrometers due to technical diffraction limitations of optical wavelength manipulation. Multidimensional printer 200 overcomes such technical limitations and provides higher resolution such as hundreds of nanometers in lateral and vertical directions in forming solid crosslinked polymer structure 210. Printing of solid crosslinked polymer structure 210 directly from liquid state of liquid composition 201 provides gel encapsulation of objects that may not be delivered inside a gel structure after fabrication with conventional methods and overcomes technical barriers of non-uniform distribution in manufacturing processes, where encapsulation is done post-gelation. Multidimensional printer 200 can encapsulate live cells for tissue engineering. Further, multidimensional printer 200 provides flexibility in resolution, size, or shape of solid crosslinked polymer structure 210 that can be made via tuning parameters that include beam energy, current, dwell time of energetic crosslinking particles 207 received by liquid composition 201. Diverse materials can be subjected to being printed to form solid crosslinked polymer structure 210 by multidimensional printer 200, wherein such material can include compositional gel material that may not be optically transparent and may not be printable with UV printing.

Multidimensional printer 200 and processes herein provide electron and x-ray lithography to be conducted in liquid state. The latter drastically increases the number of material, composites and devices to be processed and fabricated with unprecedented thickness and dimensional control.

The articles and processes herein are illustrated further by the following Example, which is non-limiting.

Example

Electron and X-ray Focused Beam Induced Crosslinking in Liquids

Conventional additive fabrication of three-dimensional (3D) provides micron to centimeters size constructs made of polymers and soft materials from photo-curable formulations suitable for optical photolithography, holographic, and stereolithography.

Polymerization and crosslink chemical reactions were initiated inside a liquid composition with focused electron beams. The beam writing was done through the thin electron/X-rays transparent membranes separating high-vacuum equipment from the volatile precursor solution. Using a hydrogel as a model soft material, in-liquid direct writing with sub 100 nm resolution was performed. Focused soft X-rays with variable photon energies provide gel crosslinking with chemical and spatial selectivity. Crosslinking in hydrogel solutions takes place at low radiation doses that are below a viability threshold for biological cells with high spatial resolution for applications in tissue micro-engineering, drugs delivery, biosensing, bio-electronics, and the like.

To deliver focused electron or soft X-ray beams to vacuum-incompatible liquid solutions and for patterning and imaging in liquids, fluidic and closed chambers were equipped with 30 nm to 50 nm thin silicon nitride (SiN) membranes to isolate the liquid solution from the vacuum of the microscope, wherein panel A of FIG. 3 shows a configuration for electrons and panel D of FIG. 3 shows a configuration for X-rays.

Figure 5:
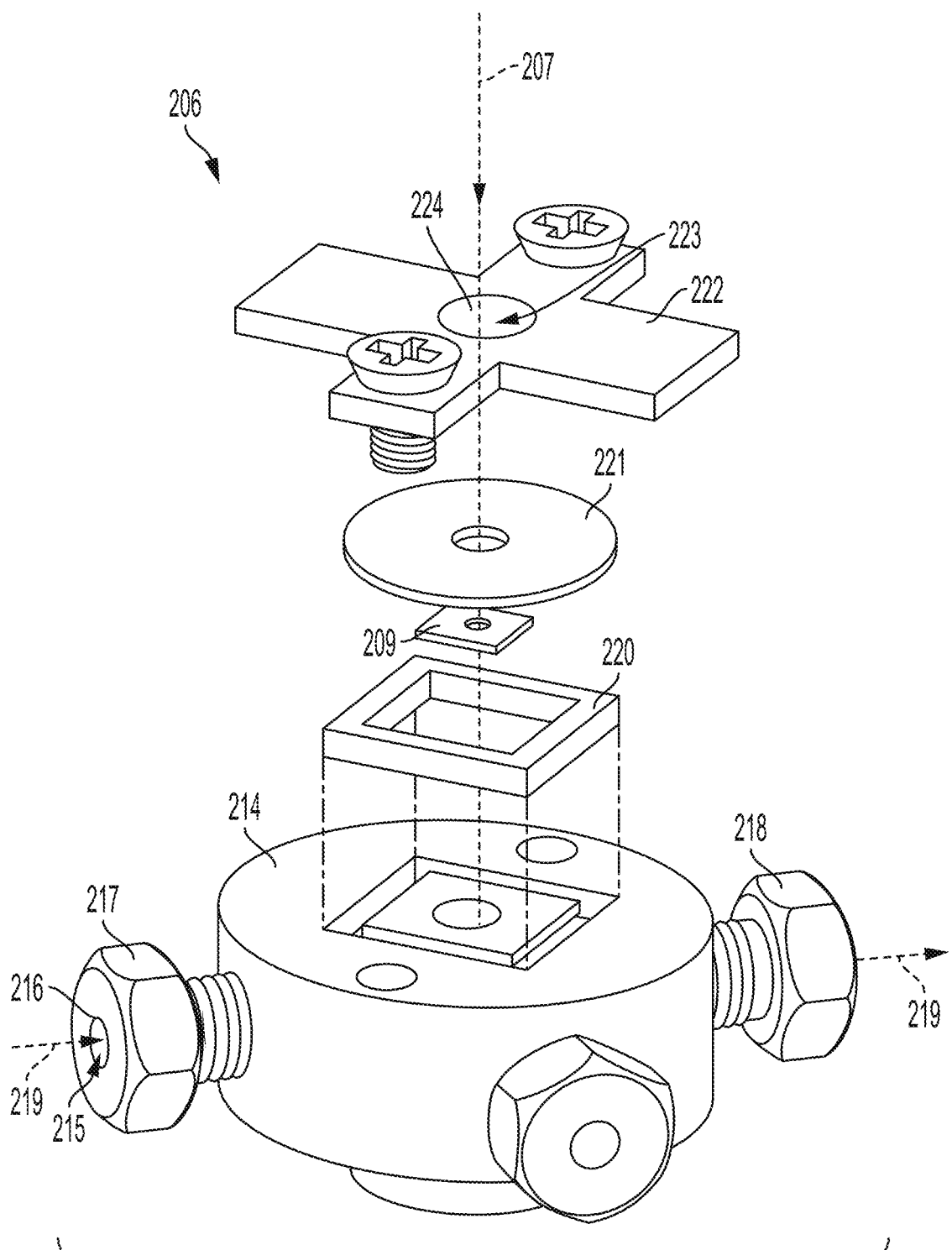
FIG. 5 shows an exploded view of the sample chamber shown in FIG. 4.
Figure 8:
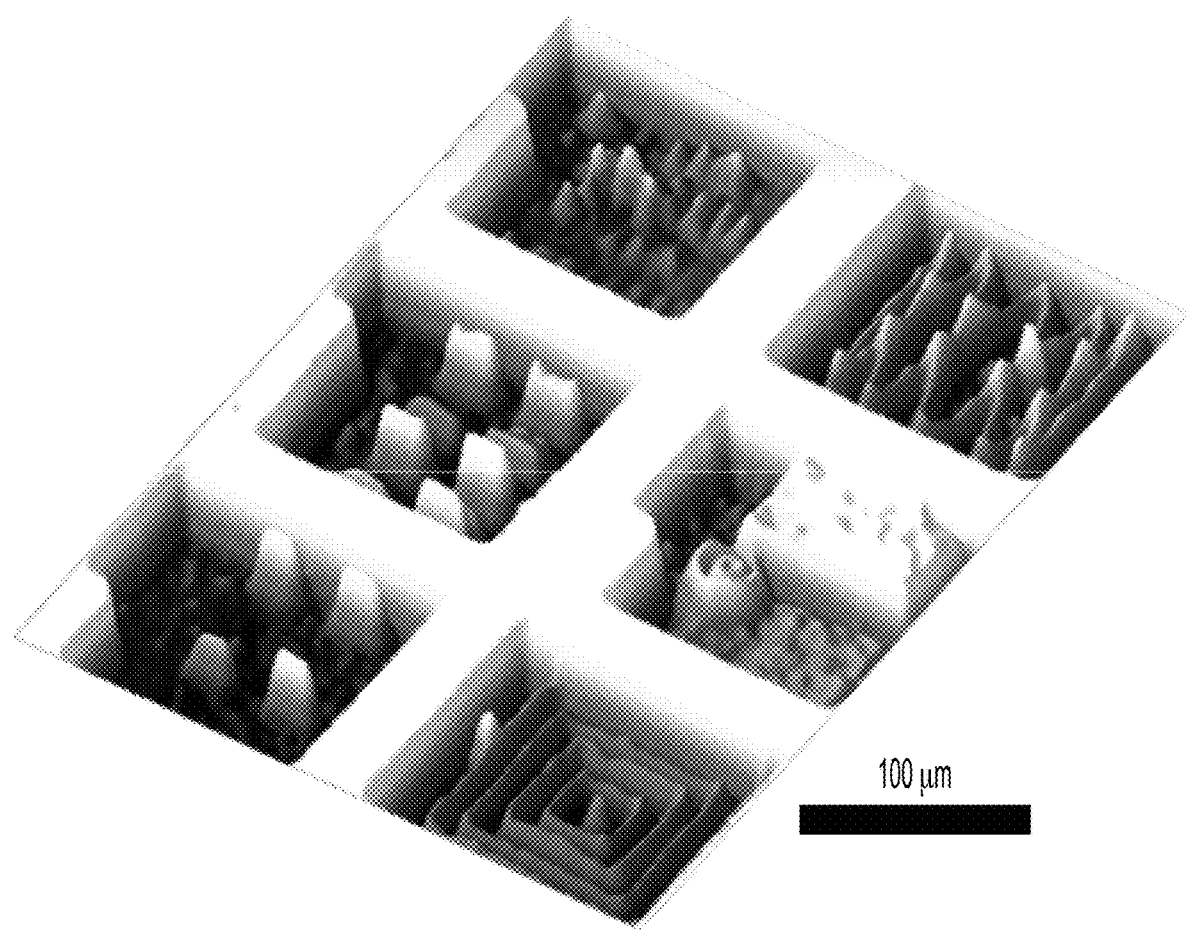
FIG. 8 shows a three-dimensional surface plot of an optical image of solid crosslinked polymer structures that were electron beam printed on a membrane.

FIG. 4, FIG. 5, and FIG. 8 show an SEM-compatible chamber and results therefrom that were used with electron focused beam-induced polymer crosslinking in volatile solutions. The chamber for X-ray studies contained about 5 microliters of enclosed hydrogel precursor solution and was smaller in size. Both chambers were equipped with a SiN/Si chip patterned with an array of nine 50 nm thick and 100 μm×100 μm wide SiN suspended membranes capable of withstanding a 1 Bar ($10^5$ Pa) pressure differential. This single-use exchangeable SiN/Si chip is vacuum-sealed against the body of the fluidic (or enclosed) cell and the interior of the chamber was filled with poly(ethylene glycol) diacrylate (PEGDA) 20% w/v aqueous solution. Nine identical membrane windows were used for writing multiple features and combinatorial data collection within a single experiment as show in FIG. 8. Arrays of rectangular and fine linear structures were printed on individual membrane windows by varying only one of the parameters: beam energy, irradiation intensity, step-size or dwell time while keeping others locked. After rinsing off the uncured solution with water, the dimensions of the cross-linked stable gel structures were inspected in the hydrated state using atomic force microscopy (AFM) and optical profilometry and more precisely after drying by SEM. By comparing the height of the same objects in their hydrated and dry state the gel's average vertical swelling ratio was estimated as a function of the polymer molecular mass, concentration of the solution and typical electron beam irradiation conditions. Such calibrations were used to estimate the size of the dried-up hydrated gel objects.

With regard to hydrogel synthesis and printing, printing was performed with a stagnant liquid setup where ca 5-10 μL of 20% w/v PEGDA (average molar mass 0.7 kg/mol, no initiator) aqueous solution was drop-casted on to Si chip with an array of nine 50 nm thick SiN membranes. The chip was bonded to supporting plate and sealed with vacuum-tight (flow) chamber with silicone rubber gasket. Inside SEM, liquid prepolymer solution was patterned through the SiN window using focused electron beam with a known amount of dose at every pixel. The experiment was repeated in another part of the 100 μm×100 μm window or at the different SiN window using a different set of irradiation parameters. After e-beam exposure, the chip was taken out of the chamber and gently rinsed in DI water to remove the uncured solution. This leaves an array of printed gel features adhered to SiN membranes. The latter were inspected in a hydrated state with AFM or optical microscopy/profilometry and/or in a dry state using SEM, AFM, EDS, XPS, μ-Raman and other characterization tools. Printing with soft X-rays was performed at ESCA microscopy beamline equipped with zone plate optics capable to focus monochromatized light to a spot 150 nm in diameter. The undulator and monochromator have been set to operate either at 526 eV or at 536 eV with the photon flux in the order of $10^9$ photons/s at 150 nm wide focal spot. The chamber equipped with the same chip with nine SiN membranes array was filled with PEGDA solution, sealed and scanned in front of the beam in a pre-programmed path to generate a required pattern.

Electrochemical delamination tests have been made using PBS-based 20% w/v PEDGA solution.

With regard to composite hydrogels, gold nanoparticles (50 nm in dia.) suspension in water was pre-concentrated by centrifuging (2000 r/min, 5 min) and was subsequently extracted and mixed with a 20% w/v PEGDA solution. The prepared composite mixture was irradiated in the liquid phase with an electron or soft X-ray beams through 50 nm SiN membrane. The chip with the printed composite gel structures was then developed in water and subsequently analyzed as described in the article and Supporting material.

With regard to live cells interfacing and proliferation printing. Caco-2 cells were thawed and cultured in DMEM (Dulbecco's Modification of Eagle's medium) with 4.5 g/L glucose and L-glutamine without sodium pyruvate for a few days. These were subsequently washed in phosphate-buffered saline solution (PBS) and DMEM. Lifting off process was carried out using 2 ml of 0.05% (w/v) trypsin-EDTA and left for 5 min to 10 min until the attached cells become mobile on the slide. Neutralization of trypsin is done by adding an equal volume of growth medium. The obtained cell suspension is concentrated by centrifuge. The cell concentrate was added to the PBS-based 20% w/v PEDGA solution and cells were allowed to adhere to the SiN membrane. For viability tests after irradiation, the crosslinked gel with encapsulated cells was rinsed in the growth medium for cell and exposed to calcein green dye in the growth medium for 1 hr. Inside the live cells, the non-fluorescent calcein is converted into green-fluorescent calcein via de-esterification of the acetoxymethyl group by the esterases only produced by a live cell.

With regard to modeling, a stack of 50 nm SiN and 20-micron thick water layer was modeled with the electron beam incident on the SiN membrane. The Monte Carlo (MC) simulations (described in the SI section) generated the trajectories and corresponding energy deposited (Gy). The parameters used to generate FIG. 2 a) were as follows: $6.25 \cdot 10^5$ electrons for a 5 nm beam diameter for 3 keV, 5 keV, 10 keV, and 20 keV primary beam energy. The energy deposition results in Gy for $6.25 \cdot 10^5$ electrons were scaled depending on the current value to obtain the rate of energy deposition (Gy/s) and fed into the radiolysis kinetics model (described in more details in the SI section). To generate results shown in FIG. 2*d*), the CFD model was executed for 3 keV primary beam, and currents current values: 50 pA, 85 pA, 125 pA, 160 pA, 200 pA and 215 pA.

Figure 9B:
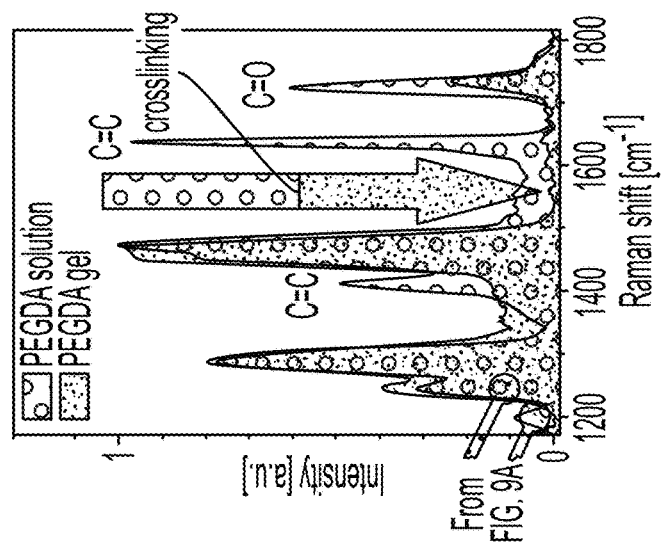
FIG. 9 shows in panel A, top facet: electron beam gelation in a liquid polymer solution through a 50 nm thick SiN membrane. Lower energy electrons generate smaller excitation volume and a finer feature size. The left facet of panel A shows a spatial distribution of energy deposition by electron beams in water, and the right facet of panel A shows direct and indirect, through radiolytic radicals R, poly(ethylene glycol) diacrylate (PEGDA) polymer crosslinking. Panel B shows decreasing C=C bonds in PEGDA solution upon irradiation with ca. $10^6$ Gy dose for crosslinking of precursor molecules. Panel C shows a comparison of energy dependence of electron and soft X-ray ionization cross sections of liquid water. Panel D shows absorbed energy doses as a function of depth for electrons at 100 pA current and 1 ms dwell time and for X-rays at $2 \times 10^9$ photons/s and 10 ms dwell time, wherein dashed vertical lines depict empirical hydrated feature sizes, and error bars are standard deviations from three separate experiments. Panel E shows an energy deposited distribution for 3 keV 200 pA electron beam in the left panel and distribution of hydroperoxyl radical concentration in the right panel.
Figure 9A:
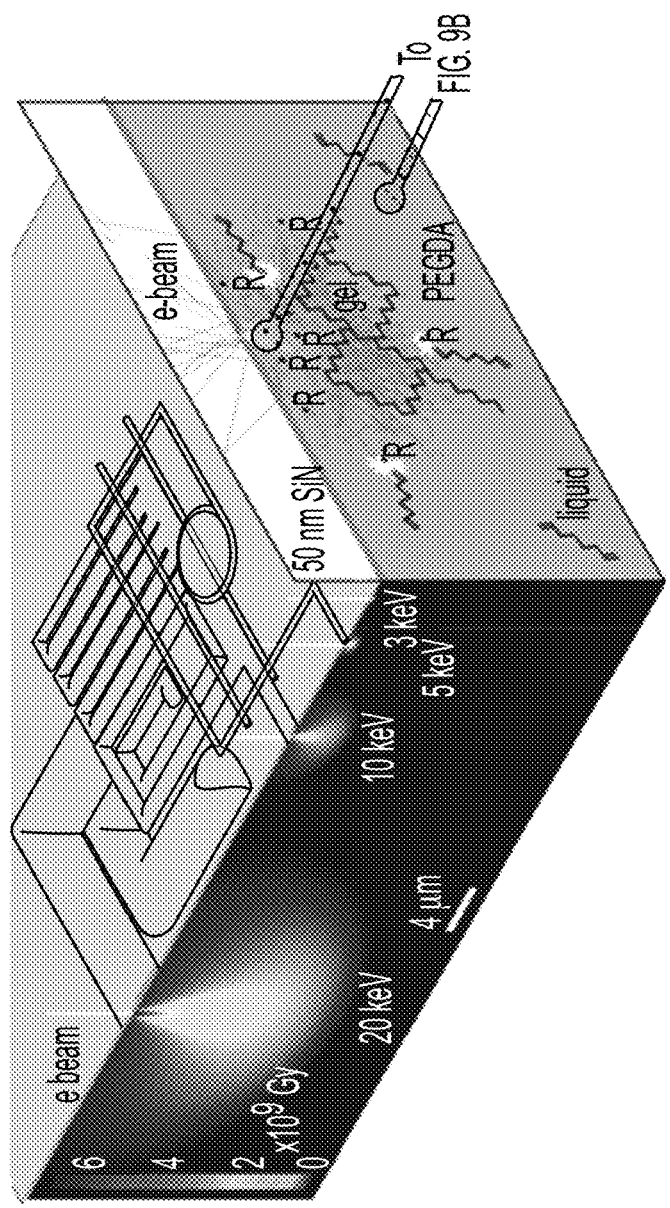

With regard to focused beam induced crosslinking process in polymer aqueous solutions, upon impinging on the liquid interface of the PEGDA aqueous solution, the electrons experience a cascade of elastic and inelastic scattering events, which slow down and broaden the beam thus creating a droplet-like highly excited interaction volume where the crosslinking of the PEGDA polymer molecules into insoluble gel matrix takes place (FIG. 9A, right facet). Without wishing to be bound by theory, radiation-induced crosslinking in polymer solutions occurs via two mechanisms: directly, by activating the reactive groups in the polymer solute with primary or secondary electrons or indirectly, by electron beam-induced solvent radiolysis that generates a variety of radicals promoting crosslinking. The partitioning between these two reaction channels depends on multiple parameters such as the solute concentration, molecular weight of the polymer, beam energy, its intensity, radical diffusion coefficient, and the like. This, in turn, provides flexibility for highly penetrating ionizing radiation with spatially homogenous excitation and diffusional profiles. Compared to broad beam irradiation conditions, focused electron or X-ray beams generate highly localized, spatially inhomogeneous radiolitic volumes where the radiation chemistry and kinetics are less explored. The comparative side-to-side µ-Raman analysis of irradiated and pristine PEDGA regions (FIG. 9B) reveals quick quenching of the 1410 cm$^{-1}$, 1640 cm$^{-1}$ C=C stretching bands upon electron irradiation, as is expected for complete crosslinking of PEGDA via abstracting hydrogen atoms and opening the carbon double bonds in its acrylate end groups predominantly by the radiolitic OH radicals.

Figure 9C:
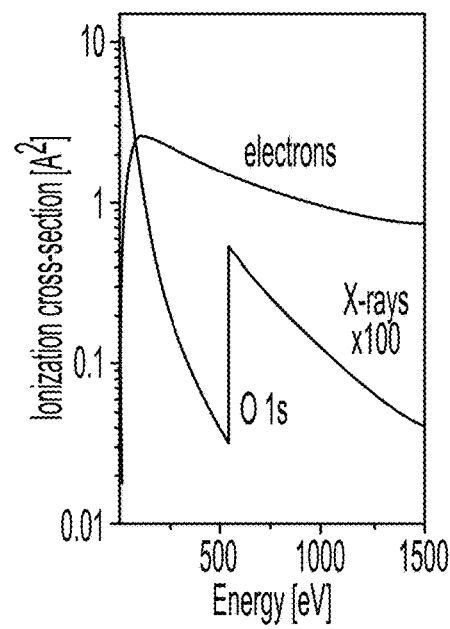

When soft X-rays trigger crosslinking, the net effect is similar, although it proceeds via different electronic excitation/relaxation pathways. X-ray photon ionize/excites the valence and core electrons of the solute and solution molecules. The relaxation of core hole proceeds primarily via emission of Auger electrons After such a de-excitation, the energy is effectively absorbed by the liquid via the same inelastic electron scattering mechanism as described above for electron beam induced crosslinking. The major differences between the electron and soft X-ray induced crosslinking, therefore, are due to their ionization cross-sections as can be seen from the liquid water example (FIG. 9C). The values of liquid water photoionization cross-section for soft X-rays (100 eV to 2000 eV) are on the average ca. 100 times smaller compared to the few keV electrons. Therefore, such X-rays can penetrate significantly deeper into the precursor solution forming gel features with larger aspect ratios and lower crosslinking densities. In addition, the electron ionization cross-section of water is a smooth function of energy (FIG. 9C), thus the range of electrons in water solution and printed feature size always increase with energy. In the case of soft X-rays however, the photoionization cross-section sharply increases at the onset of the OIs core level excitations (FIG. 9C). This chemical selectivity of the X-rays range in the solution will be used to control the aspect ratio of the printed features or chemically selective objects encapsulation.

Figure 9D:
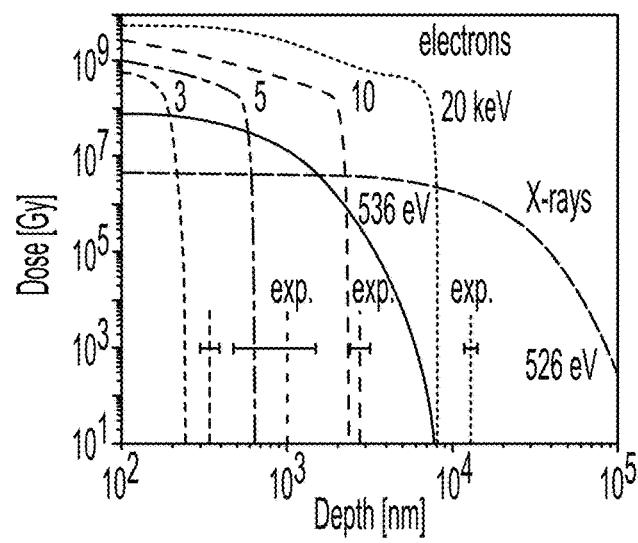

Since the crosslinking in moderately concentrated PEGDA solutions proceeds primarily via interaction with radiolytic radicals, their diffusion beyond the electron-sample interaction volume can be the feature size determining factor. To evaluate the effect of radical diffusion on crosslinking we compared the experimental feature sizes the e-beam printed in a 20% w/v PEGDA aqueous solution with the modeled ones applying the same irradiation conditions. Monte Carlo (MC) simulated spatial distributions of the radiation dose deposited in aqueous solution through a 50 nm thick SiN membrane are shown in FIG. 9D for a few different energies and a 5 nm wide electron beam. Assuming the critical energy dose for PEGDA gelation being within the range $10^3$ Gy to $10^6$ Gy, the height of stable hydrated objects can be from 200 nm for 3 kV to 8 micrometers for 20 keV electron beams (FIG. 9D).

Figure 9E:
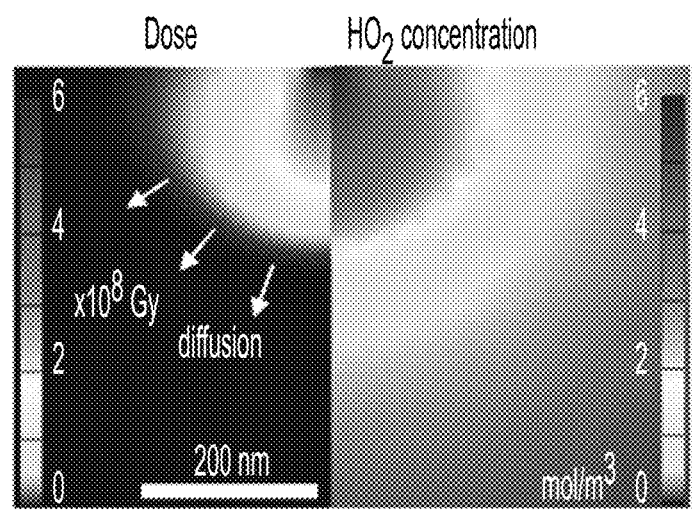

Empirical data on thicknesses of hydrated features obtained under the same conditions (dashed lines in FIG. 9D) are larger than the depths at the onset of gelation critical density obtained from Monte Carlo simulations. The latter indicates that indirect crosslinking via a runaway diffusion of radiolytic activators may indeed be responsible for the observed size increase of the printed features. To support the observation further, we adapted a kinetic radiolysis model to our SEM conditions. The numerical simulations based on this model predict a short lifetime and therefore a small runaway diffusion length (<200 nm) for the most abundant crosslinking OH radical outside the electron beam interaction volume, thus implying that there can exist other radicals with larger lifetimes that can, in principle, diffuse to longer distances before reacting out completely. One of the possible crosslinking agents particularly abundant in water under aerated conditions is hydroperoxyl radical. FIG. 9E compares the energy dose distribution upon water irradiation with 3 keV focused beam (left panel) with the corresponding $HO_2^-$ concentration profile (right panel). As can be seen, $HO_2^-$ crosslinking activator concentration remains high, well beyond the electron dose gelation threshold and therefore may account for the systematically increased size of the printed features.

With regard to printing controls, parameters tuned to control the size, shape, and sharpness of features within the individual printed layer were present. In raster scanning mode, parameters include: electron beam energy (E), dwell time ($\tau_D$) at a pixel location, step-size (L) during the scan and exposure dose D per pixel defined as $D=I_B\tau_D n/L^2$ where $I_B$ is an electron (photon) beam current (intensity) and n is number of scans.

Figure 10J:
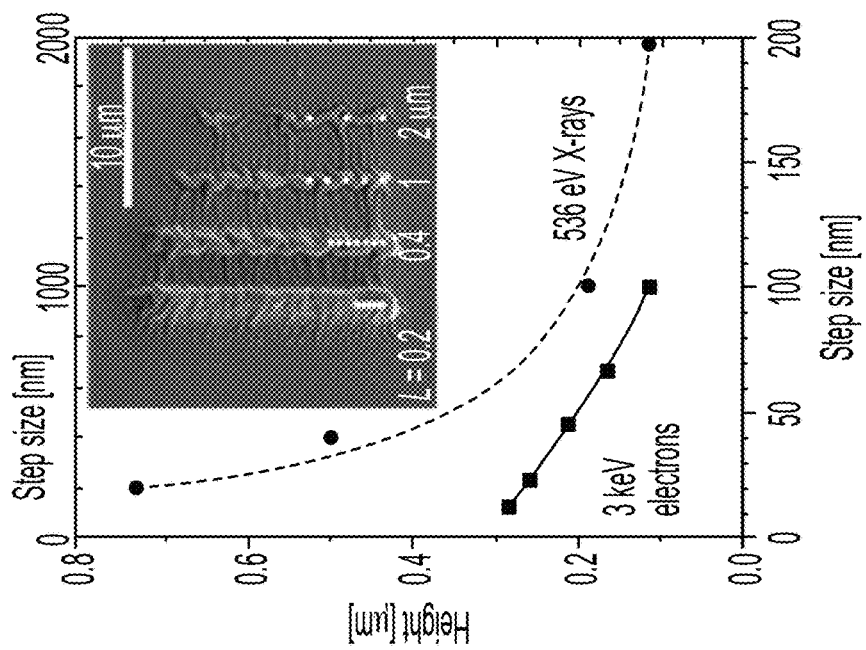
FIG. 10 shows SEM images of 3D features that were patterned with focused electron beam in panel A to E and patterned with soft X-rays in panels F and G. Numbers indicated inside each panel are energy, beam currents as photons intensities, dwell times, and step sizes used. In panel A, NIST was formed with 3 keV electrons at 100 pA and 1 ms dwell time with 10 nm pixel size. Panel B shows an annular structure formed by writing 1 µm wide ring with a radius of 10 µm. Panel C shows a curved structure, wherein a larger portion of the curve is from beam parking with a longer dwell time. Panel D shows a dome-shaped structure formed from four overlapping coaxial rings, shown in panel E, by varying electron beam energy and dose for every ring. Panel F shows letters printed with 536 eV and 150 nm wide X-ray beam with 25 ms dwell time. Photon flux was about $2\times10^7$ photons/nm$^2$ s and 100 nm step size. Panel G shows die printed with two photon energies for 13 µm base squares at 536 eV and 2.5 µm squares at 526 eV. Panels H to J show heights measured by SEM of the dry rectangular and linear structures as a function of exposure dose (panel H), dwell time (panel I) and step size (panel J) for different energies of electrons and X-rays beams. Insets show an SEM image of structure written with variable beam current (panel H), dwell time along its length using 536 eV X-rays (panel I), and step-size L using 536 eV X-rays and 3 keV electrons.
Figure 10I:
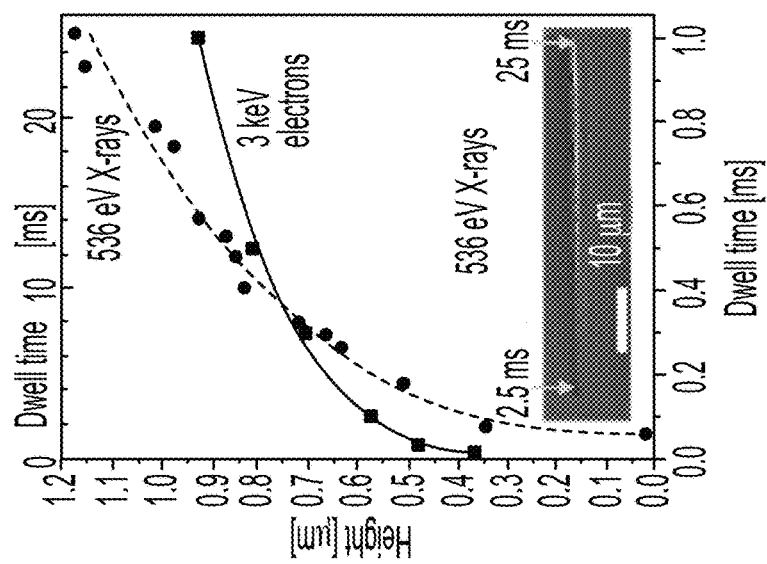
Figure 10H:
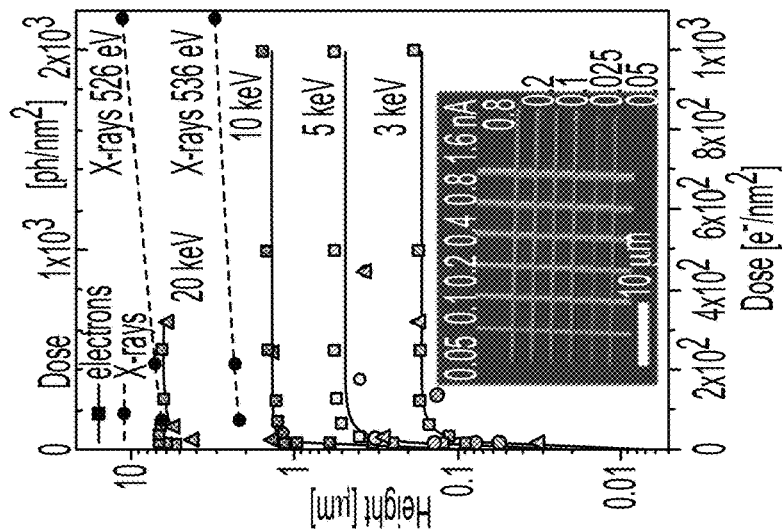

FIG. 10A-G shows 3D structures printed using in-liquid crosslinking by electrons (panels A-E) and soft X-rays (panels F, G). The primary energy of electrons determines the range of electrons in the solvent and therefore the height profiles of the printed structure ranging from ca 100 nm to ca 10 μm while varying beam energy from 3 keV to 20 keV (FIG. 10B, D). The dynamic range of heights exceeding 100 aspect ratio was achieved via beam energy variation, however, the sharpness of the features drops concomitantly with energy. The comparable aspect ratios of 3D structures can be obtained via varying only the dwell time. Different from the beam energy variations, which requires refocusing, the facile and instant modulation of the dwell time and step-size allows the fabrication of the high-aspect ratio microstructures, e.g. a flagella-like object in FIG. 10C in a single run with a writing speed of ca. 5 mm/s. Note that similar structures have been used for locomotion in liquids after being functionalized with magnetic nanoparticles. The effect of the beam intensity and writing sequence on the linear feature size and morphology can be seen in the inset of FIG. 10H. Feature size increases with the beam intensity and then saturates. This is a result of the increase and saturation of the crosslink density inside the excitation volume similarly to the radiation induced crosslinking in a dry state. Feature size can be controlled effectively via printing with different X-ray photon energies just below and above the element specific absorption edge (e.g., OIs in FIG. 9B). The example in the FIG. 10G shows that this can be performed even through an already printed feature. Compared to printing with electrons, the aspect ratio of the X-ray-induced structures can be appreciably larger similar to the deep X-ray lithography results on solid films. In addition, the crosslink density of X-ray printed hydrogel structures was noticeably lower compared to their e-beam counterparts reflecting significant surface rippling of the features upon drying. FIG. 10H-J quantifies the measured heights of the crosslinked dried gel features as a function of each one of these parameters with others being unchanged. In addition to the apparent increase of the feature size with electron beam energy (FIG. 10H), the height variation with exposure dose has characteristic fast rise followed by saturation behavior what was also commonly observed in dry films. Critical dose threshold (on the order of 1 $e^-/nm^2$) provides through-membrane crosslinking of a stable gel structure. While the dose increase does not affect the dimensions of the interaction volume in water, it expands the boundary at which the critical concentration of crosslinking radicals can be maintained. The same is valid for the feature heights increase with the dwell-time (FIG. 10I). Step-size becomes a rather important parameter when the beam is rastered across the sample surface. By increasing the step-size and therefore the pixel area, one can tune the overlap between the interaction volumes (diffusion zones) of individual adjacent voxels, thus reducing or increasing the effective thickness (and width) of the printed feature. An important distinction between the electron and soft X-ray beam writing used in this study is the size of the probe: electron beam has a diameter of ca. 5 nm, while for X-rays it is ca. 150 nm in our setups. On the other hand, the effective diameter of the interaction volume of a few keV electron beam is appreciably larger (see FIG. 9A) compared to one for soft X-rays. Therefore, for X-rays, the formation of corrugated/discontinuous patterns can be observed as soon as the step-size becomes larger than 150 nm (see inset in FIG. 10J). On the contrary, few keV electron beams generate continuous patterns, for step-size values even larger than 100 nm.

For printing applications, dwell-time and step-size can be independent irradiation parameters to control the size and crosslink density of raster printed gel structures. Unlike the beam energy and intensity, these two parameters are decoupled in the SEM controls and can be tuned during the scanning without refocusing. In the case of the e-beam printing, the lateral and longitudinal resolution of the resultant features are coupled and are proportional to each other (FIG. 9A). As one intensifies any of the parameters: beam energy, intensity, dwell time, both the width and height of the pattern increase. Finally, the smallest feature size and maximum resolution for SEM based gelation can be achieved via lowering the energy of electrons that can penetrate through the SiN window. We were able to routinely write ca. 150 nm thin and 100 nm wide gel lines through a 50 nm SiN window using 3 keV electron beam energy. Sub-100 nm features are attainable if thinner membranes are used.

With regard to in-liquid direct writing for layer-by-layer printing with electron beams, sequentially crosslinked features 1 and 2 are shown in FIG. 11A that overlap and have double-exposed region (OER) as a second layer. OER can have an increased thickness compared to a parent structure. Since the feature size depends on the accumulated dose (see FIG. 10H), this height difference can vary from its maximum value at very low doses to zero at doses above ca. $10^2$ $e^-/nm^2$. Moreover, the size and shape of the resultant structure (including OER) may not depend on the writing sequence (i.e. shape$_{12}$=shape$_{21}$). For in-liquid crosslinking, layer-by-layer log-pile structures (FIG. 11B) were printed in PEGDA solution and studied as a function of writing sequence, electron energy, and dose.

SEM images in FIG. 11C show log-pile structures patterned side-by-side with low (left) and high (right side) doses. As expected, due to complete crosslinking along the length of the structures, the high-dose structure does not show any noticeable increase of the thickness of nods in comparison to the thickness of the regular bar. The morphology of the structure printed in liquid with a low dose, however, exhibit a noticeable dependence on the writing sequence and does not follow an expected commutative exposure rule characteristic for solid resists (e.g. shape$_{23}\ne$shape$_{43}$). We assume that in-liquid electron beam writing proceeds in a different way compared to solid resist and the mechanical stress induced by densification of the OER upon sequential writing leads to mechanical lifting and eventually delamination of the prior-printed construct (FIG. 11C, left panel).

Delamination of the printed layer from the optical windows has been a speed limiting factor of the first bottom-up 3D laser printers. This has been resolved via implementation of continuous liquid interface production technology which employed quenching of the polymer crosslinking at the liquid-window interface with a controlled through-the-window delivery of molecular oxygen inhibitor. Along these lines, electrochemically driven pH variations in PEG solutions have be used to reduce the crosslinking density of hydrogel to improve their cellular adhesion and permeability. The role of the electrochemically generated inhibitors on the size and adhesion of the electron beam printed structures was investigated. The supporting SiN membrane was coated with a few tens of nanometers thick Pt layer defined as the working electrode in a two-electrode electrochemical cell filled with PEGDA/PBS aqueous electrolyte. The anodic potential of the working electrode was adjusted to near the onset of water splitting reaction (FIG. 11B). SEM images in FIG. 1D show two log-pile constructs printed using the same irradiation parameters but with (right panel) and without (left pane) anodic potential applied to the conducting membrane with respect to the counter electrode. The drastic reduction of the size and adhesion of the printed construct (right panel) can be observed, which might be explained by the electrochemical increase of the near electrode concertation of the crosslinking inhibitors like $O_2$ that hamper beam induced crosslinking process. Cathodic potential, on the other hand, leads to electrochemical polymerization of the PEGDA solution at the membrane electrode and overwhelms the beam-induced prints. The electrochemical quenching/promoting of the PEGDA crosslinking not only provides an additional control of the e-beam printed feature size but has a direct consequence for the additive fabrication of overlying structures in a layer-by-layer manner.

With regard to composite hydrogels as plasmonic microsensors, hydrogel applications has broadened via synthesis of composite formulations for the rational engineering of optical, electrical, mechanical, and magnetic properties for numerous applications. Fabrication of composite organic hydrogels can be classified as: (i) in situ ones where functional inclusions (e.g. nanoparticles) or precursors are pre-mixed in the prepolymer solution and become stabilized in the hydrogel during the crosslinking process, whereas (ii) ex situ techniques typically involve an inclusion impregnation process, applied after the crosslinking of the host matrix. In situ encapsulation offers the advantages of embedding objects independently of their size, homogeneously across the bulk, while the post-crosslinking impregnation depends on surface-to-bulk diffusion of chemicals into the gel's matrix which is often hampered for the objects larger than gel's mesh size. FIG. 12A (panels 1and 2) shows in-liquid entrapping of nanoparticles and via focused e-beam induced cross-linking of nanoparticles suspension. Due to facile coupling of the mechanical optical, chemical and electrical properties of such composite gels to external stimuli they become a common platform for numerous sensor designs. FIG. 11B shows a plasmonic humidity microsensor e-beam printed out of PEGDA/50 nm Au nanoparticles suspension. The broadband light source excites the localized surface plasmon resonances (LSPR) in the selected gel-imbedded nanoparticle assembly (see inset in the FIG. 11C). The scattered light is collected in the reflection dark field mode and the shift of the LSPR maximum L is determined spectroscopically as a function of the humidity level above the sensor. The observed blue shift of the $\lambda_m$ with increase of the humidity level (FIG. 11C) is presumably due to a combination of two factors: reduction of the gel refractive index with humidity and weakening of the dipole-dipole coupling between the adjacent nanoparticles in the aggregate (which scales as $(D/d)^3$) upon gel matrix swelling, here D is Au NP diameter and d is the interparticle distance. The size of the e-beam gelated composite in this particular study was ca. 100 µm×100 µm×5 µm, however the plasmonic hot spots were located inside Au NP assembly that is only ca. 500 nm wide (see insets in FIG. 11C).

With regard to cellular interfacing with hydrogel patches, computer-brain interfacing with neural probes or cardiac cellular electrophysiology can involve development of soft microelectrode arrays that match mechanical chemical and electrical properties of the individual live cells. PEG-based hydrogels are prospective soft interface electrode materials due to their biocompatibility or adjustable elastic moduli and ionic conductance. Sub-micron indexing of life cells with PEGDA microelectrodes can be made. To compensate for small polymerization cross-section and preserve sufficient reaction rate inside the mesoscopic voxel, high concentrations of cytotoxic photo-initiators can be use that may compromise the biocompatibility of the electrodes. To overcome these shortcomings, we employ in-liquid gel focused electron (X-ray) beam crosslinking technique for cellular interfacing. In addition to highest lateral resolution of the membrane patching and flexible electrodes patterning, the advantage such an approach lays in a nanometer depth control of the electron range and crosslinking density across the irradiated patch such as desired degree of electrical and gentle mechanical contact can be achieved at the very cellular membrane-gel electrode interface. PEGDA contact formation can be administered on a live cell before its membrane irreversibly degrades. The extent of radiation damage of the biological objects (cells) during electron beam-induced PEGDA crosslinking is not well known and generated reactive radiolytic species like OH', O⁻, and $H_2O_2$ at high concentrations are known to be detrimental to the cells. Critical dose values span from ca. $10^{-3}$ e⁻/nm² to ca. $10^2$ e⁻/nm² that are considered acceptable for live mammalian cells, yeasts and other microorganisms. Such a margin manifests a fundamental challenge of high-resolution electron microscopy of live cells as well as the variance in live/dead criteria applied. PEGDA crosslinking threshold dose is on the order of 1 e⁻/nm² in our setup and can be reduced by at least an order of magnitude if higher molecular weight PEG is used. Since the imaging during crosslinking (which usually leads to high irradiation dose) is not a requirement, the encapsulation of live microorganisms using our in-liquid lithography can be feasible. The test process flow is depicted in FIG. 12A, panels 1, 3, 4. Once a prepolymer solution with premixed and proximal to SiN membrane live cells was exposed to electrons, the cross-linked gel with trapped/interfaced cells was tested with standard calcein-AM cell viability assay. Live cells uptake the non-fluorescent calcein-AM ester. Inside the living cell, ester reacts with cytosolic esterases, which convert it into a green-fluorochrome: calcein to which cellular membrane is not permeable. Bright-field optical image in FIG. 12D shows a SiN window containing cell-laden PEGDA solution after exposure to 10 keV primary beam with an average exposure dose of 8 e⁻/nm² (absorbed dose ca $3 \times 10^6$ Gy). Fluorescent microscopy image of gel-immobilized cells in the FIG. 12E complements FIG. 12D and indicates (i) that cells B-E do produce fluorescent calcein after encapsulation; (ii) calcein distribution remains confined within the cellular borders indicating the integrity of cellular membrane and (iii) some of the cells (cell A in the FIG. 12E) appear dark implying its necrosis, while the rest of the cells apparently survive the interfacing procedure. Although local absorption dose at the point of beam incidence can be few orders of magnitude higher than the cell's lethal dose limit, interfacing of the life cells with PEGDA electrode may be due to radiation damage that is mainly localized within a submicron gap of solution between the cellular and SiN membranes (FIG. 12A). Cells that are poorly adhered or floating in solution ca micron away from the SiN membrane see a significantly diluted load of radiolitic species. Moreover, the majority of the reactive species produced by the beam becomes scavenged during gel crosslinking process what, therefore effectively reduce the concentration of toxic species seen by the cells.

Spatially controlled crosslinking inside liquid polymer solutions employing scanning electron and soft X-ray microscopy occurred. Gel interfacing of live cells, fabrication of a composite hydrogel plasmonic device, and 3D printing of model hydrogel structures with a sub-micrometer resolution can be made. Threshold dose required for electron beam-induced PEGDA cross-linking in a liquid state can be on the order of 1 $e^-/nm^2$ and explored the effect of diffusion of radiolitic species and other empirically adjustable and tunable parameters such as electrons (or X-rays) energy, beams intensity, exposure time, electrochemically driven pH value and the like on the resolution and size of the features formed. High spatial resolution printing of a large class of hydrogels precursor solutions in the liquid state can also be extended to gas phase polymerization and offers unique advantages in shape, size and precision compared to traditional dry gel lithography and can complement the existing multiphoton polymerization methods. The multidimensional printer 200 can be implemented in a high vacuum, environmental SEM, atmospheric SEM, synchrotrons or laboratory-based X-ray microscope, and the like. The tunability of X-ray energy at synchrotrons opens an additional opportunity to conduct element specific 3D gel printing in solutions relevant to biomedical, soft micro-robotics, electrochemical and other applications. Moreover, the combination of our method with the recently proposed implosive fabrication technique can result in nanometer-scale 3D printing.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A multidimensional printer for making a multidimensional structure from a liquid composition, the multidimensional printer comprising:
   an energetic crosslinking particle source that produces energetic crosslinking particles;
   a vacuum chamber in vacuum communication with the energetic crosslinking particle source and that receives the energetic crosslinking particles from the energetic crosslinking particle source and communicates the energetic crosslinking particles to a membrane;
   the membrane in particle communication with the vacuum chamber and comprising a barrier layer and a transmission layer disposed on the barrier layer, wherein a portion of the membrane has some of the transmission layer in an absence of the barrier layer for transmission of the energetic crosslinking particles through the transmission layer without being obstructed by the barrier layer, such that the membrane:
      receives the energetic crosslinking particles from the vacuum chamber;
      blocks, by the barrier layer, the energetic crosslinking particles from being further communicated in the multidimensional printer; and
      transmits, by the transmission layer, the energetic crosslinking particles for further communication in the multidimensional printer; and
   a sample chamber in communication with the membrane and that:
      receives a liquid composition that comprises a solvent and a plurality of polymers disposed in the solvent, the polymers comprising a cross-linkable moiety;
      receives the energetic crosslinking particles communicated from the transmission layer of the membrane; and
      subjects the cross-linkable moieties of the polymers to the energetic crosslinking particles such that portions of the polymers proximate to the cross-linkable moieties subjected to the energetic crosslinking particles crosslink to form a solid crosslinked polymer structure,
   wherein the membrane isolates a vacuum of the vacuum chamber from vapor of the liquid composition in the sample chamber; and
   a shadow mask interposed between the energetic crosslinking particle source and the membrane and that receives the energetic crosslinking particles from the energetic crosslinking particle source and communicates the energetic crosslinking particles to the membrane, wherein the shadow mask selectively controls transmission of the energetic crosslinking particles through the shadow mask via apertures disposed in the shadow mask.

2. The multidimensional printer of claim 1, further comprising a sample translation stage disposed in the sample chamber and in mechanical communication with the solid crosslinked polymer structure produced from crosslinking the polymers by the energetic crosslinking particles, wherein the sample translation stage translates away from the membrane, toward the membrane, or laterally with respect to the membrane so that a two-dimension or three-dimensional size or shape of the solid crosslinked polymer structure can be spatially controlled during formation of the solid crosslinked polymer structure from the polymers.

3. The multidimensional printer of claim 1, wherein the energetic crosslinking particles comprise electrons.

4. The multidimensional printer of claim 1, wherein the energetic crosslinking particles comprise X-rays.

5. The multidimensional printer of claim 1, wherein the energetic crosslinking particles comprise poly(ethylene glycol) diacrylate.

6. The multidimensional printer of claim 1, wherein a spatial resolution of forming the solid crosslinked polymer structure depends on a size of an interaction volume between the polymers and the energetic crosslinking particles and energy of the energetic crosslinking particles.

7. The multidimensional printer of claim 1, wherein the spatial resolution is tunable and is from 10 nm to 90 μm.

8. The multidimensional printer of claim 1, wherein the membrane comprises a barrier layer comprising silicon and a transmission layer comprising silicon nitride disposed on the barrier layer.

9. The multidimensional printer of claim 1, further comprising:
the liquid composition that comprises the solvent and the plurality of polymers disposed in the solvent, wherein the polymers comprise the cross-linkable moiety.

10. The multidimensional printer of claim 1, further comprising:
the multidimensional structure comprising the solid crosslinked polymer structure disposed on the membrane, the solid crosslinked polymer structure obtained from the polymer in response to crosslinking the polymer via the cross-linkable moiety.

11. The multidimensional printer of claim 9, wherein solute is disposed in the liquid composition such that solute receives energetic crosslinking particles and locally crosslinks the polymers proximate to the solute.

12. The multidimensional printer of claim 11, wherein the solute comprises quantum dots, nanoparticles, or a combination comprising at least one of the foregoing solutes.

13. The multidimensional printer of claim 10, wherein, during formation of the solid crosslinked polymer structure, the liquid composition in the sample chamber is a static liquid volume or is subject to fluid flow through the sample chamber.

14. The multidimensional printer of claim 9, wherein the liquid composition is subjected to relative rastering of the energetic crosslinking particles in the liquid composition for two-dimensional patterning of the polymers to form the solid crosslinked polymer structure having a selected two-dimensional pattern.

15. The multidimensional printer of claim 14, wherein the liquid composition, in contact with the solid crosslinked polymer structure having the selected two-dimensional pattern, is subjected to modulation of an energy or intensity of the energetic crosslinking particles in the liquid composition such that addition of polymers to the solid crosslinked polymer structure provide a selected three-dimensional geometry to the solid crosslinked polymer structure with the two-dimensional pattern.

16. The multidimensional printer of claim 14, wherein the liquid composition, in contact with the solid crosslinked polymer structure having the selected two-dimensional pattern, receives additional polymers for crosslinking in presence of the energetic crosslinking particles such that additional polymers are crosslinked to the solid crosslinked polymer structure to provide a selected three-dimensional geometry to the solid crosslinked polymer structure with the two-dimensional pattern.

* * * * *